(12) United States Patent
Sanderson et al.

(10) Patent No.: US 8,168,652 B2
(45) Date of Patent: May 1, 2012

(54) INHIBITORS OF AKT ACTIVITY

(75) Inventors: Philip E. Sanderson, Valley Forge, PA (US); Mark E. Layton, Harleysville, PA (US); Kevin J. Rodzinak, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/255,757

(22) PCT Filed: Mar. 3, 2010

(86) PCT No.: PCT/US2010/025990
§ 371 (c)(1),
(2), (4) Date: Sep. 9, 2011

(87) PCT Pub. No.: WO2010/104705
PCT Pub. Date: Sep. 16, 2010

(65) Prior Publication Data
US 2011/0319443 A1 Dec. 29, 2011

Related U.S. Application Data

(60) Provisional application No. 61/159,460, filed on Mar. 12, 2009.

(51) Int. Cl.
*A61K 31/44* (2006.01)
*C07D 471/02* (2006.01)
(52) U.S. Cl. .................................. 514/300; 546/112
(58) Field of Classification Search .............. 546/122; 514/300
See application file for complete search history.

(56) References Cited

U.S. PATENT DOCUMENTS

| | | |
|---|---|---|
| 2004/0116432 A1 | 6/2004 | Carling et al. |
| 2004/0143117 A1 | 7/2004 | Barnett et al. |
| 2005/0159422 A1 | 7/2005 | Lindsley et al. |
| 2005/0222155 A1 | 10/2005 | Bilodeau et al. |
| 2005/0288294 A1 | 12/2005 | Duggan et al. |
| 2006/0030564 A1 | 2/2006 | Owens et al. |
| 2006/0205765 A1 | 9/2006 | Bilodeau et al. |
| 2006/0270673 A1 | 11/2006 | Duggan et al. |
| 2007/0043001 A1 | 2/2007 | Bilodeau et al. |
| 2007/0082906 A1 | 4/2007 | Bilodeau et al. |
| 2007/0142388 A1 | 6/2007 | Duggan et al. |
| 2007/0149536 A1 | 6/2007 | Lindsley et al. |
| 2007/0254901 A1 | 11/2007 | Bilodeau et al. |
| 2008/0009507 A1 | 1/2008 | Cosford et al. |
| 2008/0015212 A1 | 1/2008 | Barnett et al. |
| 2008/0280899 A1 * | 11/2008 | Bilodeau et al. ........... 514/234.5 |
| 2008/0287457 A1 | 11/2008 | Arruda et al. |
| 2009/0062327 A1 | 3/2009 | Chen et al. |
| 2009/0253734 A1 | 10/2009 | Kelly, III et al. |
| 2010/0022573 A1 | 1/2010 | Layton et al. |
| 2010/0075970 A1 | 3/2010 | Bilodeau et al. |
| 2010/0222321 A1 | 9/2010 | Armstrong et al. |

FOREIGN PATENT DOCUMENTS

| | | |
|---|---|---|
| WO | 2009148887 A1 | 12/2009 |
| WO | 2009148916 A1 | 12/2009 |
| WO | 2010088177 A1 | 8/2010 |
| WO | 2010104705 A1 | 9/2010 |
| WO | 2010104933 A1 | 9/2010 |
| WO | 2010114780 A1 | 10/2010 |

\* cited by examiner

*Primary Examiner* — Binta Robinson
(74) *Attorney, Agent, or Firm* — Matthew A. Leff; Yong Zhao; David A. Muthard

(57) ABSTRACT

The instant invention provides for substituted naphthyridine compounds that inhibit Akt activity. In particular, the compounds disclosed selectively inhibit one or two of the Akt isoforms. The invention also provides for compositions comprising such inhibitory compounds and methods of inhibiting Akt activity by administering the compound to a patient in need of treatment of cancer.

8 Claims, No Drawings

INHIBITORS OF AKT ACTIVITY

REFERENCE TO SEQUENCE LISTING SUBMITTED ELECTRONICALLY

The sequence listing of the present application is being submitted electronically via EFS-Web as an ASCII formatted sequence listing with a file name "MRLONC00012USPCT-SEQTXT-09SEP2011.txt", creation date of Sep. 8, 2011 and a size of 3,554 bytes. This sequence listing submitted via EFS-Web is part of the specification and is herein incorporated by reference in its entirety.

BACKGROUND OF THE INVENTION

The present invention relates to substituted naphthyridine compounds which are inhibitors of the activity of one or more of the isoforms of the serine/threonine kinase, Akt (also known as PKB; hereinafter referred to as "Akt"). The present invention also relates to pharmaceutical compositions comprising such compounds and methods of using the instant compounds in the treatment of cancer.

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science,* 281:1322-1326 (1998)). The execution of programmed cell death is mediated by caspase-1 related proteinases, including caspase-3, caspase-7, caspase-8 and caspase-9 etc (Thornberry et al. *Science,* 281:1312-1316 (1998)).

The phosphatidylinositol 3'-OH kinase (PI3K)/Akt pathway appears important for regulating cell survival/cell death (Kulik et al. *Mol. Cell. Biol.* 17:1595-1606 (1997); Franke et al, *Cell,* 88:435-437 (1997); Kauffmann-Zeh et al. *Nature* 385:544-548 (1997) Hemmings *Science,* 275:628-630 (1997); Dudek et al., *Science,* 275:661-665 (1997)). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns(3,4,5)-P3), which in turn binds to, and promotes the activation of, the serine/threonine kinase Akt, which contains a pleckstrin homology (PH)-domain (Franke et al *Cell,* 81:727-736 (1995); Hemmings *Science,* 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt mutants abolish survival-promoting activities of these growth factors or cytokines. It has been previously disclosed that inhibitors of PI3K (LY294002 or wortmannin) blocked the activation of Akt by upstream kinases. In addition, introduction of constitutively active PI3K or Akt mutants promotes cell survival under conditions in which cells normally undergo apoptotic cell death (Kulik et al. 1997, Dudek et al. 1997).

Three members of the Akt subfamily of second-messenger regulated serine/threonine protein kinases have been identified and termed Akt1/PKBα, Akt2/PKBβ, and Akt3/PKBγ (hereinafter referred to as "Akt1", "Akt2" and "Akt3"), respectively. The isoforms are homologous, particularly in regions encoding the catalytic domains. Akts are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt. The current model of Akt activation proposes recruitment of the enzyme to the membrane by 3'-phosphorylated phosphoinositides, where phosphorylation of the regulatory sites of Akt by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1 occurs on two regulatory sites, $Thr^{308}$ in the catalytic domain activation loop and on $Ser^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2 and Akt3. The upstream kinase, which phosphorylates Akt at the activation loop site has been cloned and termed 3'-phosphoinositide dependent protein kinase 1 (PDK1). PDK1 phosphorylates not only Akt, but also p70 ribosomal S6 kinase, p90RSK, serum and glucocorticoid-regulated kinase (SGK), and protein kinase C. The upstream kinase phosphorylating the regulatory site of Akt near the carboxy terminus has not been identified yet, but recent reports imply a role for the integrin-linked kinase (ILK-1), a serine/threonine protein kinase, or autophosphorylation.

Analysis of Akt levels in human tumors showed that Akt2 is overexpressed in a significant number of ovarian (J. Q. Cheng et al. *Proc. Natl. Acad. Sci. U.S.A.* 89:9267-9271 (1992)) and pancreatic cancers (J. Q. Cheng et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. No specific PDK1 inhibitors have been disclosed. Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

It is an object of the instant invention to provide novel compounds that are inhibitors of Akt.

It is also an object of the present invention to provide pharmaceutical compositions that comprise the novel compounds that are inhibitors of Akt.

It is also an object of the present invention to provide a method for treating cancer that comprises administering such inhibitors of Akt activity.

SUMMARY OF THE INVENTION

The instant invention provides for substituted naphthyridine compounds that inhibit Akt activity. In particular, the compounds disclosed selectively inhibit one or two of the Akt isoforms. The invention also provides for compositions comprising such inhibitory compounds and methods of inhibiting Akt activity by administering the compound to a patient in need of treatment of cancer.

DETAILED DESCRIPTION OF THE INVENTION

The compounds of the instant invention are useful in the inhibition of the activity of the serine/threonine kinase Akt. In a first embodiment of this invention, the inhibitors of Akt activity are illustrated by the Formula A:

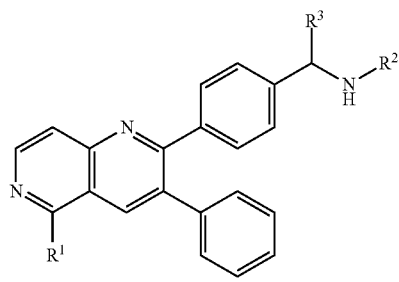

A wherein:

$R^1$ is aryl, heteroaryl or heterocyclyl;

$R^2$ is a $(C_1-C_{10})$alkyl or heterocyclyl which are optionally substituted with from one to three substituents selected from OH, $O(C_1-C_6)$alkyl, phenyl and heterocyclyl, wherein said phenyl is optionally substituted with from one to three substituents selected from OH; and $R^3$ is a $(C_1-C_3)$alkyl or hydrogen;

or a pharmaceutically acceptable salt or a stereoisomer thereof.

In a second embodiment of this invention, the inhibitors of Akt activity are illustrated by the Formula A, wherein:

$R^1$ is aryl or heteroaryl;

$R^2$ is a $(C_1-C_{10})$alkyl which is optionally substituted with from one to three substituents selected from OH, $O(C_1-C_6)$ alkyl and phenyl, wherein said phenyl is optionally substituted with from one to three substituents selected from OH; and $R^3$ is methyl or hydrogen;

or a pharmaceutically acceptable salt or a stereoisomer thereof.

In a third embodiment of this invention, the inhibitors of Akt activity are illustrated by the Formula A, wherein:

$R^1$ is 4-pyrazolyl;

$R^2$ is a $(C_1-C_{10})$alkyl or heterocyclyl which are optionally substituted with from one to three substituents selected from OH, $O(C_1-C_6)$alkyl, phenyl and heterocyclyl, wherein said phenyl is optionally substituted with from one to three substituents selected from OH; and $R^3$ is methyl or hydrogen;

or a pharmaceutically acceptable salt or a stereoisomer thereof.

In a fourth embodiment of this invention, the inhibitors of Akt activity are illustrated by the Formula A, wherein:

$R^1$ is 4-pyrazolyl;

$R^2$ is a $(C_1-C_{10})$alkyl which is optionally substituted with from one to three substituents selected from OH, $O(C_1-C_6)$ alkyl and phenyl, wherein said phenyl is optionally substituted with from one to three substituents selected from OH; and $R^3$ is methyl or hydrogen;

or a pharmaceutically acceptable salt or a stereoisomer thereof.

In a fifth embodiment of this invention, the inhibitors of Akt activity are illustrated by the Formula A, wherein:

$R^1$ is 4-pyrazolyl;

$R^2$ is a $(C_1-C_{10})$alkyl which is optionally substituted with from one to three substituents selected from OH and $O(C_1-C_6)$alkyl; and $R^3$ is methyl or hydrogen;

or a pharmaceutically acceptable salt or a stereoisomer thereof.

In a sixth embodiment of this invention, the inhibitors of Akt activity are illustrated by the Formula A, wherein:

$R^1$ is 4-pyrazolyl;

$R^2$ is a $(C_1-C_{10})$alkyl which is optionally substituted with from one to three substituents selected from OH and $OCH_3$; and $R^3$ is methyl or hydrogen;

or a pharmaceutically acceptable salt or a stereoisomer thereof.

Specific compounds of the instant invention include:
2,2-dimethyl-3-({4-[3-phenyl-5-(1H-pyrazol-4-yl)-1,6-naphthyridin-2-yl]benzyl}amino)propan-1-ol (1-4);
3-({4-[3-phenyl-5-(1H-pyrazol-4-yl)-1,6-naphthyridin-2-yl]benzyl}amino)propan-1-ol (1-5);
{1-[({4-[3-phenyl-5-(1H-pyrazol-4-yl)-1,6-naphthyridin-2-yl]benzyl}amino)methyl]cyclobutyl}methanol (1-6);
{1-[({4-[3-phenyl-5-(1H-pyrazol-4-yl)-1,6-naphthyridin-2-yl]benzyl}amino)methyl]cyclopentyl}methanol (1-7);
{1-[({4-[3-phenyl-5-(1H-pyrazol-4-yl)-1,6-naphthyridin-2-yl]benzyl}amino)methyl]cyclohexyl}methanol (1-8);
4-({4-[3-phenyl-5-(1H-pyrazol-4-yl)-1,6-naphthyridin-2-yl]benzyl}amino)butan-1-ol (1-9);
2,2-dimethyl-N-{4-[3-phenyl-5-(1H-pyrazol-4-yl)-1,6-naphthyridin-2-yl]benzyl}propan-1-amine (1-10);
2-({4-[3-phenyl-5-(1H-pyrazol-4-yl)-1,6-naphthyridin-2-yl]benzyl}amino)ethanol (1-11);
[(1R,2S)-2-({4-[3-phenyl-5-(1H-pyrazol-4-yl)-1,6-naphthyridin-2-yl]benzyl}amino) cyclohexyl]methanol (1-12);
(2S)-1-methoxy-3-({4-[3-phenyl-5-(1H-pyrazol-4-yl)-1,6-naphthyridin-2-yl]benzyl}amino)propan-2-ol (1-13);
1-[(2S)-1,4-dioxan-2-yl]-N-{4-[3-phenyl-5-(1H-pyrazol-4-yl)-1,6-naphthyridin-2-yl]benzyl}methanamine (1-14);

2-methyl-N-{4-[3-phenyl-5-(1H-pyrazol-4-yl)-1,6-naphthyridin-2-yl]benzyl}propan-1-amine (1-15);
1-cyclopropyl-N-{4-[3-phenyl-5-(1H-pyrazol-4-yl)-1,6-naphthyridin-2-yl]benzyl}methenamine (1-16);
N-{4-[3-phenyl-5-(1H-pyrazol-4-yl)-1,6-naphthyridin-2-yl]benzyl}cyclopentanamine (1-17);
[(1S,2R)-2-({4-[3-phenyl-5-(1H-pyrazol-4-yl)-1,6-naphthyridin-2-yl]benzyl}amino)cyclohexyl]methanol (1-18);
N-{4-[3-phenyl-5-(1H-pyrazol-4-yl)-1,6-naphthyridin-2-yl]benzyl}-1H-indol-5-amine (1-19);
3-[2-({4-[3-phenyl-5-(1H-pyrazol-4-yl)-1,6-naphthyridin-2-yl]benzyl}amino)ethyl]phenol (1-20);
4-[2-({4-[3-phenyl-5-(1H-pyrazol-4-yl)-1,6-naphthyridin-2-yl]benzyl}amino)ethyl]phenol (1-21);
4-[1-hydroxy-2-({4-[3-phenyl-5-(1H-pyrazol-4-yl)-1,6-naphthyridin-2-yl]benzyl}amino)propyl]phenol (1-22);
4-[(1R,2S)-1-hydroxy-2-({4-[3-phenyl-5-(1H-pyrazol-4-yl)-1,6-naphthyridin-2-yl]benzyl}amino)propyl]phenol (1-23); and
(2,2-dimethyl-3-{[(1R)-1-{4-[3-phenyl-5-(1H-pyrazol-4-yl)-1,6-naphthyridin-2-yl]phenyl}ethyl]amino}propan-1-ol (2-6);
or a pharmaceutically acceptable salt or stereoisomer thereof.

Specific salts of the compounds of the instant invention include:
3-hydroxy-N-{4-[3-phenyl-5-(1H-pyrazol-4-yl)-1,6-naphthyridin-2-yl]benzyl}propan-1-aminium trifluoroacetate (1-5);
[1-(hydroxymethyl)cyclobutyl]-N-{4-[3-phenyl-5-(1H-pyrazol-4-yl)-1,6-naphthyridin-2-yl]benzyl}methanaminium trifluoroacetate (1-6);
[1-(hydroxymethyl)cyclopentyl]-N-{4-[3-phenyl-5-(1H-pyrazol-4-yl)-1,6-naphthyridin-2-yl]benzyl}methanaminium trifluoroacetate (1-7);
[1-hydroxymethyl)cyclohexyl]-N-{4-[3-phenyl-5-(1H-pyrazol-4-yl)-1,6-naphthyridin-2-yl]benzyl}methanaminium trifluoroacetate (1-8);
N-{4-[3-phenyl-5-(1H-pyrazol-4-yl)-1,6-naphthyridin-2-yl]benzyl}-1H-indol-5-aminium trifluoroacetate (1-19);
2-(3-hydroxyphenyl)-N-{4-[3-phenyl-5-(1H-pyrazol-4-yl)-1,6-naphthyridin-2-yl]benzyl}ethanaminium trifluoroacetate (1-20);
2-(4-hydroxyphenyl)-N-{4-[3-phenyl-5-(1H-pyrazol-4-yl)-1,6-naphthyridin-2-yl]benzyl}ethanaminium chloride (1-21);
1-hydroxy-1-(4-hydroxyphenyl)-N-{4-[3-phenyl-5-(1H-pyrazol-4-yl)-1,6-naphthyridin-2-yl]benzyl}propan-2-aminium trifluoroacetate (1-22); and
(1R,2S)-1-hydroxy-1-(4-hydroxyphenyl)-N-{4-[3-phenyl-5-(1H-pyrazol-4-yl)-1,6-naphthyridin-2-yl]benzyl}propan-2-aminium trifluoroacetate (1-23);
or a stereoisomer thereof.

Specific compounds of the instant invention include:
2,2-dimethyl-3-({4-[3-phenyl-5-(1H-pyrazol-4-yl)-1,6-naphthyridin-2-yl]benzyl}amino)propan-1-ol (1-4);
3-({4-[3-phenyl-5-(1H-pyrazol-4-yl)-1,6-naphthyridin-2-yl]benzyl}amino)propan-1-ol (1-5);
{1-[({4-[3-phenyl-5-(1H-pyrazol-4-yl)-1,6-naphthyridin-2-yl]benzyl}amino)methyl]cyclobutyl}methanol (1-6);
{1-[({4-[3-phenyl-5-(1H-pyrazol-4-yl)-1,6-naphthyridin-2-yl]benzyl}amino)methyl]cyclopentyl}methanol (1-7);
{1-[({4-[3-phenyl-5-(1H-pyrazol-4-yl)-1,6-naphthyridin-2-yl]benzyl}amino)methyl]cyclohexyl}methanol (1-8);
4-({4-[3-phenyl-5-(1H-pyrazol-4-yl)-1,6-naphthyridin-2-yl]benzyl}amino)butan-1-ol (1-9);
2,2-dimethyl-N-{4-[3-phenyl-5-(1H-pyrazol-4-yl)-1,6-naphthyridin-2-yl]benzyl}propan-1-amine (1-10);
2-({4-[3-phenyl-5-(1H-pyrazol-4-yl)-1,6-naphthyridin-2-yl]benzyl}amino)ethanol (1-11);
[(1R,2S)-2-({4-[3-phenyl-5-(1H-pyrazol-4-yl)-1,6-naphthyridin-2-yl]benzyl}amino)cyclohexyl]methanol (1-12);
(2S)-1-methoxy-3-({4-[3-phenyl-5-(1H-pyrazol-4-yl)-1,6-naphthyridin-2-yl]benzyl}amino)propan-2-ol (1-13);
2-methyl-N-{4-[3-phenyl-5-(1H-pyrazol-4-yl)-1,6-naphthyridin-2-yl]benzyl}propan-1-amine (1-15);
1-cyclopropyl-N-{4-[3-phenyl-5-(1H-pyrazol-4-yl)-1,6-naphthyridin-2-yl]benzyl}methanamine (1-16);
N-{4-[3-phenyl-5-(1H-pyrazol-4-yl)-1,6-naphthyridin-2-yl]benzyl}cyclopentanamine (1-17);
[(1S,2R)-2-({4-[3-phenyl-5-(1H-pyrazol-4-yl)-1,6-naphthyridin-2-yl]benzyl}amino)cyclohexyl]methanol (1-18); and
(2,2-dimethyl-3-{[(1R)-1-{4-[3-phenyl-5-(1H-pyrazol-4-yl)-1,6-naphthyridin-2-yl]phenyl}ethyl]amino}propan-1-ol (2-6);
or a pharmaceutically acceptable salt or stereoisomer thereof.

A compound of the instant invention is:
2,2-dimethyl-3-({4-[3-phenyl-5-(1H-pyrazol-4-yl)-1,6-naphthyridin-2-yl]benzyl}amino)propan-1-ol (1-4);
or a pharmaceutically acceptable salt thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted.

This invention is also intended to encompass pro-drugs of the compounds disclosed herein. A prodrug of any of the compounds can be made using well known pharmacological techniques.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "$(C_1-C_{10})$alkyl" is intended to include branched, straight-chain, cyclic and spirocyclic saturated aliphatic hydrocarbon groups having the specified number of carbon atoms. For example, $C_1-C_{10}$, as in "$(C_1-C_{10})$alkyl" is defined to include groups having 1, 2, 3, 4, 5, 6, 7, 8, 9 or 10 carbons in a linear, branched, cyclic or spirocyclic arrangement. Further, the compounds of the instant invention provide examples that include branched, straight-chain, cyclic and spirocyclic moieties and are encompassed by the "$(C_1-C_{10})$alkyl" definition.

As used herein, "alkyl" is intended to include branched and straight-chain saturated aliphatic hydrocarbon groups having the specified number of carbon atoms. For example, $C_1-C_6$, as in "$(C_1-C_6)$alkyl" is defined to include groups having 1, 2, 3, 4, 5 or 6 carbons in a linear or branched arrangement. For example, "$(C_1-C_6)$alkyl" specifically includes methyl, ethyl, n-propyl, i-propyl, n-butyl, t-butyl, i-butyl, pentyl, hexyl, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

In an embodiment, "aryl" means, phenyl and naphthyl.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteraoaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

In an embodiment, "heteroaryl" means pyridinyl, pyrimidinyl, pyrazolyl, thiazolyl, oxazolyl, isoxazolyl, indolyl, pyrrolyl, thiadiazolyl, oxadiazolyl, thienyl, furanyl, quinolinyl and isoforms thereof.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" or "heterocyclyl" means, benzoimidazolyl, benzoimidazolonyl, benzofuranyl, benzofurazanyl, benzopyrazolyl, benzotriazolyl, benzothiophenyl, benzoxazolyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

In an embodiment, "heterocycle" or "heterocyclyl" means, indolyl, and 1,4-dioxanyl.

In an embodiment, $R^1$ is aryl or heteroaryl.

In an embodiment, $R^1$ is aryl or heteroaryl, optionally substituted with from one to three substituents selected from OH, halo, $(C_1-C_6)$alkyl and $O(C_1-C_6)$alkyl.

In an embodiment, $R^2$ is a $(C_1-C_{10})$alkyl which is optionally substituted with from one to three substituents selected from OH, $O(C_1-C_6)$alkyl and phenyl, wherein said phenyl is optionally substituted with from one to three substituents selected from OH.

In an embodiment, $R^2$ is a $(C_1-C_{10})$alkyl which is optionally substituted with from one to three substituents selected from OH and $O(C_1-C_6)$alkyl.

In an embodiment, $R^3$ is H.

Included in the instant invention is the free form of compounds of Formula A, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula A. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TPA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the instant invention are inhibitors of the activity of Akt and are thus useful in the treatment of cancer, in particular cancers associated with irregularities in the activity of Akt and downstream cellular targets of Akt. Such cancers include, but are not limited to, ovarian, pancreatic, breast and prostate cancer, as well as cancers (including glioblastoma) where the tumor suppressor PTEN is mutated (Cheng et al., *Proc. Natl. Acad. Sci.* (1992) 89:9267-9271; Cheng et al., *Proc. Natl. Acad. Sci.* (1996) 93:3636-3641; Bellacosa et al., *Int. J. Cancer* (1995) 64:280-285; Nakatani et al., *J. Biol. Chem.* (1999) 274:21528-21532; Graff, *Expert. Opin. Ther. Targets* (2002) 6(1):103-113; and Yamada and Araki, *J. Cell Science.* (2001) 114:2375-2382; Mischel and Cloughesy, *Brain Pathol.* (2003) 13(1):52-61).

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: non-small cel lung, bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, colorectal, lung, non-small cell lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal, lung and non-small cell lung.

Cancers that may be treated by the compounds, compositions and methods of the invention include: breast, colon, (colorectal) and lung (non-small cell lung).

Cancers that may be treated by the compounds, compositions and methods of the invention include: lymphoma and leukemia.

The compounds of the instant invention are useful for the treatment of breast cancer.

The compounds of the instant invention are useful for the treatment of prostate cancer.

Akt signaling regulates multiple critical steps in angiogenesis. Shiojima and Walsh, *Circ. Res.* (2002) 90:1243-1250. The utility of angiogenesis inhibitors in the treatment of cancer is known in the literature, see J. Rak et al. *Cancer Research*, 55:4575-4580, 1995 and Dredge et al., *Expert Opin. Biol. Ther.* (2002) 2(8):953-966, for example. The role of angiogenesis in cancer has been shown in numerous types of cancer and tissues: breast carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5): 871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol. Ther.* (2002) 2(8):953-966). Thus, the Akt inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research*, 61: 3206-3211 (2001)). The Akt inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hyperinsulinism.

The compounds of the invention are also useful in preparing a medicament that is useful in treating the diseases described above, in particular cancer.

In an embodiment of the invention, the instant compound is a selective inhibitor whose inhibitory efficacy is dependent on the PH domain. In this embodiment, the compound exhibits a decrease in in vitro inhibitory activity or no in vitro inhibitory activity against truncated Akt proteins lacking the PH domain.

In a further embodiment, the instant compound is selected from the group of a selective inhibitor of Akt1, a selective inhibitor of Akt2 and a selective inhibitor of both Akt1 and Akt2.

In another embodiment, the instant compound is selected from the group of a selective inhibitor of Akt1, a selective inhibitor of Akt2, a selective inhibitor of Akt3 and a selective inhibitor of two of the three Akt isoforms.

In another embodiment, the instant compound is a selective inhibitor of all three Akt isoforms, but is not an inhibitor of one, two or all of such Akt isoforms that have been modified to delete the PH domain, the hinge region or both the PH domain and the hinge region.

The present invention is further directed to a method of inhibiting Akt activity which comprises administering to a mammal in need thereof a pharmaceutically effective amount of the instant compound.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and a lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycet-anol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, iffy protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, 1LX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[di- amine-platinum(II)]bis[diamine(chloro)platinum (II)]tetra-chloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 742-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefitr, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, raripimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[(3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_v\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92106079, 92112151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylene®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron AC)); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

The compounds of the instant invention are useful for treating cancer in combination with taxanes.

The compounds of the instant invention are useful for treating cancer in combination with docetaxel (Taxotere®).

The compounds of the instant invention are useful for treating cancer in combination with vorinostat (Zolinza®).

The compounds of the instant invention are useful for treating cancer in combination with the aurora kinase inhibitor, MK-0457.

The compounds of the instant invention are useful for treating cancer in combination with the mTor inhibitor, AP 23573.

The compounds of the instant invention are useful for treating cancer in combination with the IGF1R inhibitor, MK-0646.

The compounds of the instant invention are useful for treating cancer in combination with satraplatin.

The compounds of the instant invention are useful for treating cancer in combination with lapatinib (Tykerb®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer, In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

Abbreviations used in the description of the chemistry and in the Examples that follow are: AEBSF (p-aminoethylbenzenesulfonyl fluoride); BSA (bovine serum albumin); Cal (calculated); Calc'd (calculated); CDCl3 (chloroform-d); DCE (dichloroethane); DCM (dichloromethane); DMSO (dimethyl sulfoxide); DTT (dithiothreitol); EDTA (ethylenediamine-tetra-acetic acid); EGTA (ethylene-glycol-tetra-acetic acid); Eq (equivalents); EtOAc (ethyl acetate); HOAc (acetic acid); HPLC (high-performance liquid chromatography); HRMS (high resolution mass spectrum); LCMS (liquid chromatograph-mass spectrometer); LRMS (low resolution mass spectrum); MeCN (acetonitrile); MeOH (methanol); NaHCO3 (sodium bicarbonate); Na2SO4 (sodium sulfate); Na(OAc)3BH (sodium triacetoxyborohydride); NMP (N-methylpyrrolidinone); NMR (nuclear magnetic resonance); PBS (phosphate buffered saline); PCR (polymerase chain reaction); Pd(Ph3P)2Cl2 (bis-triphenylphosphinepalladium dichloride); Sat (saturated); TBAF (tetrabutylammonium fluoride); THF (tetrahydrofuran); and TFA (trifluoroacteic acid).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes does not necessarily correlate to that used in the claims and often, for clarity, a single substituent is shown attached to the compound where multiple substituents are allowed under the definitions of Formula A herein above.

Synopsis of Reaction Schemes

Utilizing the following general Reaction Schemes, Reaction Schemes I-II, one of ordinary skill in the art would be able to synthesize the substituted bicyclic molecules (see Formula A) of the instant invention. The requisite intermediates are in some cases commercially available or can be prepared according to literature procedures.

As illustrated in Reaction Scheme I, a chloronaphthyridine derivative I-1 is functionalized using methods familiar to one of ordinary skill in the art, in this case with a heteroaryl ring using a palladium-catalyzed coupling reaction, to give naphthyridine I-2 (see Formula A, $R^1$ is aryl or heteroaryl). Unmasking of the aldehyde through removal of an acetal protecting group under acidic conditions provides aldehyde I-3. Functionalization of aldehyde I-3 in the presence of an amine and a reducing agent, such as sodium triacetoxyborohydride, generates I-4 see Formula A, $R^2$).

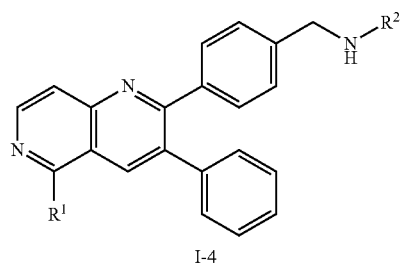

I-4

As illustrated in Reaction Scheme II, an alternative reaction sequence involves preparation of chloronaphthyridine II-3 from aldehyde II-1 first by forming imine II-2 using tert-butyl-sulfinamide, then reacting imine II-2 with nucleophiles such as methylmagnesium bromide. Chloronaphthyridine II-3 can be functionalized with a heteroaryl ring using a palladium-catalyzed coupling reaction and the amine deprotected under acidic conditions, such as hydrochloric acid, to give amine II-4 (see Formula A, $R^1$ is aryl or heteroaryl). Functionalization of amine II-4 in the presence of an aldehyde under reducing conditions, such as sodium triacetoxyborohydride provides II-5 (see Formula A, $R^2$).

Reaction Scheme I

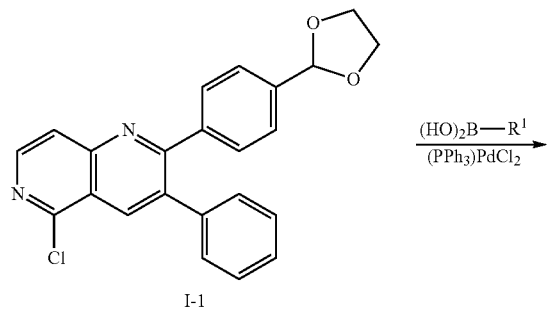

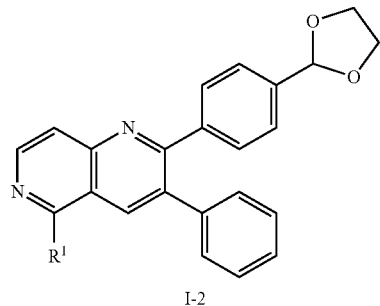

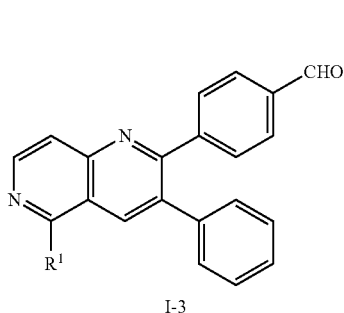

Reaction Scheme II

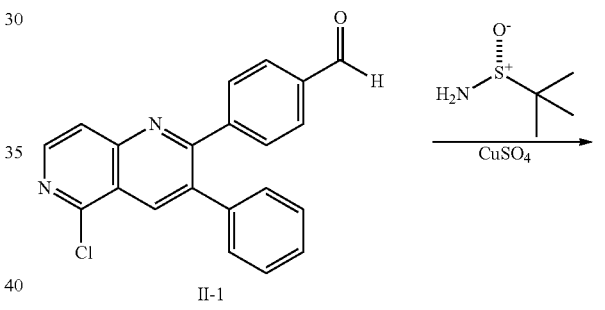

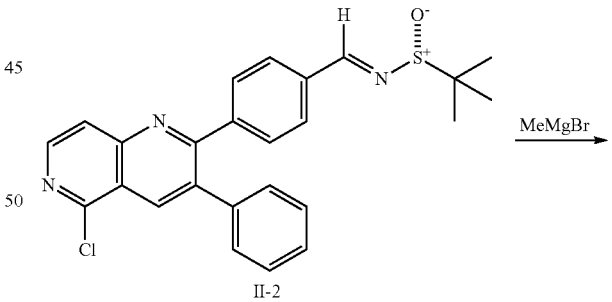

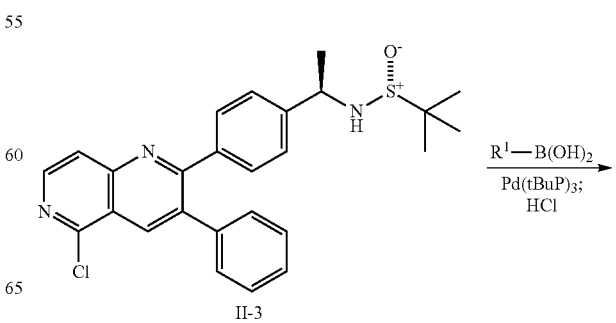

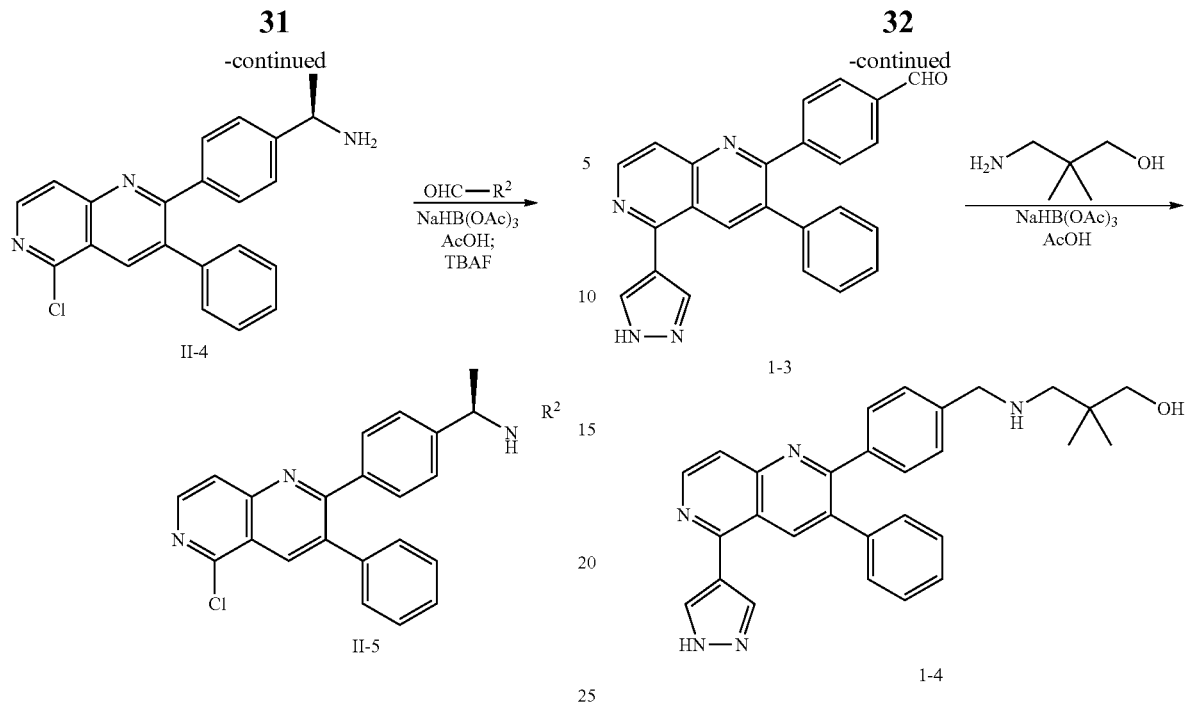

EXAMPLES

Examples and schemes provided are intended to assist in a further understanding of the invention. Particular materials employed, species and conditions are intended to be further illustrative of the invention and do not limit the reasonable scope thereof.

SCHEME 1

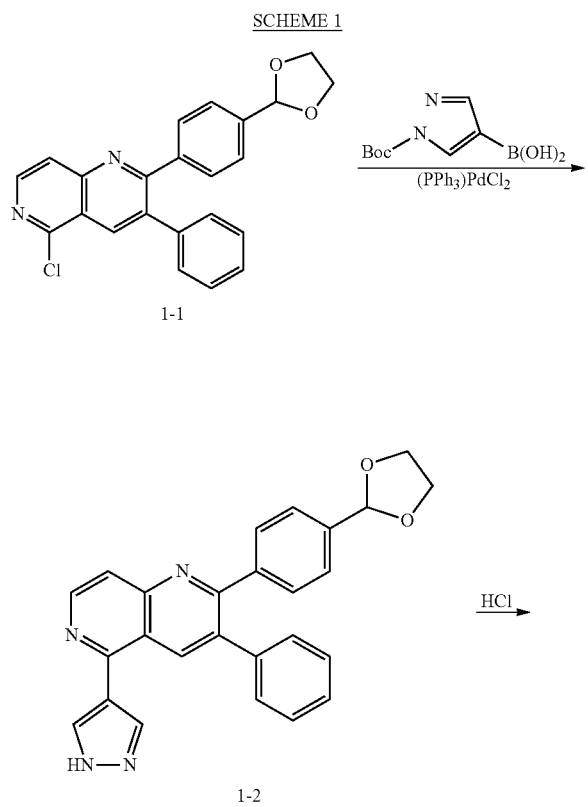

2,2-dimethyl-3-({4-[3-phenyl-5-(1H-pyrazol-4-yl)-1,6-naphthyridin-2-yl]benzyl}amino)propan-1-ol (1-4)

2-[4-(1,3-dioxolan-2-yl)phenyl]-3-phenyl-5-(1H-pyrazol-4-yl)-1,6-naphthyridine (1-2)

To a solution of 5-chloro-2-[4-(1,3-dioxolan-2-yl)phenyl]-3-phenyl-1,6-naphthyridine (1-1, Reference: WO2006135627A2, Dec. 21, 2006) (1.7 g, 4.2 mmol) in DMF (100 mL) was added tert-butyl 4-(4,4,5,5-tetramethyl-1,3,2-dioxaborolan-2-yl)-1H-pyrazole-1-carboxylate (2.5 g, 8.6 mmol), cesium carbonate (4.2 g, 13 mmol) and Pd(Ph$_3$P)$_2$Cl$_2$ (0.030 g, 0.042 mmol). The reaction mixture was heated at 100° C. under an atmosphere of N$_2$ for 1 hour. The reaction was cooled to room temperature, poured into saturated sodium bicarbonate and extracted with ethyl acetate. The combined organic layers were dried over sodium sulfate, filtered and concentrated under vacuum. Purification by silica gel chromatography (EtOAc in hexane) gave 2-[4-(1,3-dioxolan-2-yl)phenyl]-3-phenyl-5-(1H-pyrazol-4-yl)-1,6-naphthyridine (1-2) as a white solid. MS (M+H)$^+$: calculated 421.47; found 421.51

4-[3-phenyl-5-(1H-pyrazol-4-yl)-1,6-naphthyridin-2-yl]benzaldehyde (1-3)

To a solution of 2-[4-(1,3-dioxolan-2-yl)phenyl]-3-phenyl-5-(1H-pyrazol-4-yl)-1,6-naphthyridine (1-2) (1.0 g, 2.4 mmol) in NMP (25 mL) was added 6N HCl (10 mL). The reaction was heated at 80° C. for 1 hour. The reaction mixture was cooled to room temperature, slowly quenched into saturated sodium bicarbonate and extracted with ethyl acetate. The combined organic layers were dried over sodium sulfate, filtered and concentrated under vacuum to give 4-[3-phenyl-5-(1H-pyrazol-4-yl)-1,6-naphthyridin-2-yl]benzaldehyde (1-3) as a white solid. MS (M+H)$^+$: calculated 377.42; found 377.51

2,2-dimethyl-3-({4-[3-phenyl-5-(1H-pyrazol-4-yl)-1,6-naphthyridin-2-yl]benzyl}amino)propan-1-ol (1-4)

To a solution of 4-[3-phenyl-5-(1H-pyrazol-4-yl)-1,6-naphthyridin-2-yl]benzaldehyde (1-3) (0.11 g, 0.29 mmol) in NMP (10 mL) was added 3-amino-2,2-dimethylpropan-1-ol (0.030 g, 0.29 mmol) and acetic acid (0.026 g, 0.43 mmol). After stirring at room temperature for 2 hours, sodium triacetoxyborohydride (0.092 g, 0.43 mmol) was added and the reaction was stirred at room temperature for 15 hours. The reaction was poured into saturated sodium bicarbonate and extracted with ethyl acetate. The combined organic layers were dried over sodium sulfate, filtered and concentrated under vacuum. Purification by reverse phase chromatography (5-95% acetonitrile/water/0.1% TFA; Water Sunfire C18) gave 2,2-dimethyl-3-({4-[3-phenyl-5-(1H-pyrazol-4-yl)-1,6-naphthyridin-2-yl]benzyl}amino)propan-1-ol (1-4) as a off white solid. HRMS (M+H)$^+$: calculated 464.2207; found 464.2194

The compounds in Table 1 were prepared according to the Reaction Schemes and Scheme 1.

TABLE 1

| Cmp | Structure | Name | MS m/z (M + H): calc'd | MS m/z (M + H): observed |
|---|---|---|---|---|
| 1-5 | 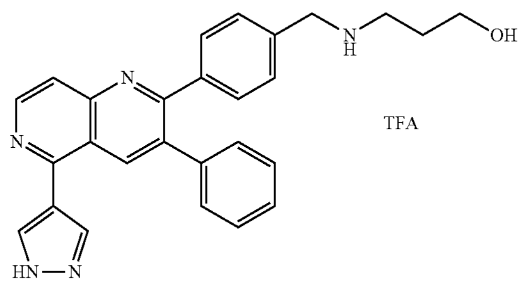 | 3-hydroxy-N-{4-[3-phenyl-5-(1H-pyrazol-4-yl)-1,6-naphthyridin-2-yl]benzyl}propan-1-aminium trifluoroacetate | 436.5339 | 436.5332 |
| 1-6 | 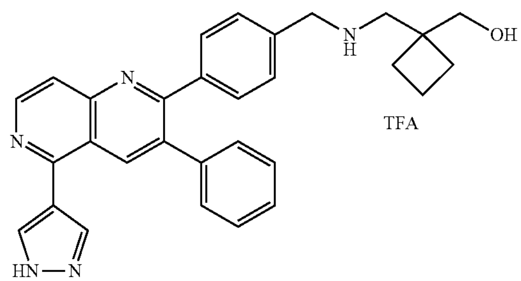 | [1-(hydroxymethyl)cyclobutyl]-N-{4-[3-phenyl-5-(1H-pyrazol-4-yl)-1,6-naphthyridin-2-yl]benzyl}methanaminium trifluoroacetate | 476.6094 | 476.6016 |
| 1-7 | 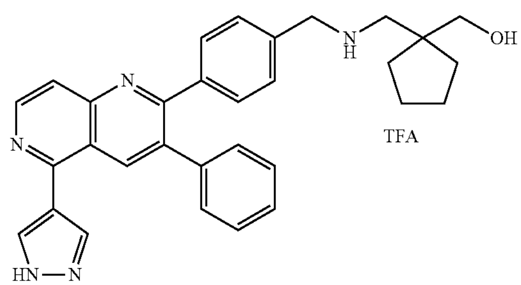 | [1-(hydroxymethyl)cyclopentyl]-N-{4-[3-phenyl-5-(1H-pyrazol-4-yl)-1,6-naphthyridin-2-yl]benzyl}methanaminium trifluoroacetate | 490.6339 | 490.6326 |
| 1-8 | 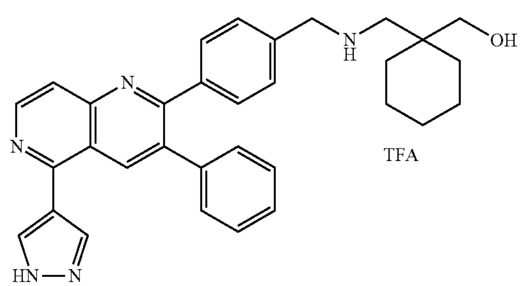 | [1-(hydroxymethyl)cyclohexyl]-N-{4-[3-phenyl-5-(1H-pyrazol-4-yl)-1,6-naphthyridin-2-yl]benzyl}methanaminium trifluoroacetate | 504.6570 | 504.6572 |

TABLE 1-continued

| Cmp | Structure | Name | MS m/z (M + H): calc'd | MS m/z (M + H): observed |
|---|---|---|---|---|
| 1-9 | 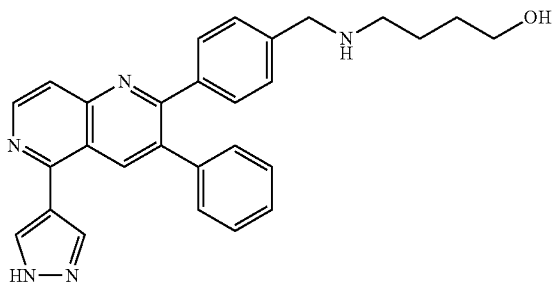 | 4-({4-[3-phenyl-5-(1H-pyrazol-4-yl)-1,6-naphthyridin-2-yl]benzyl}amino)butan-1-ol | 450.5615 | 450.5601 |
| 1-10 | 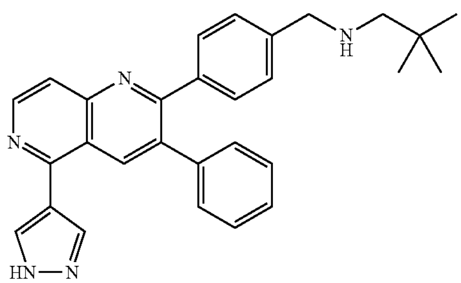 | 2,2-dimethyl-N-{4-[3-phenyl-5-(1H-pyrazol-4-yl)-1,6-naphthyridin-2-yl]benzyl}propan-1-amine | 448.5983 | 448.5986 |
| 1-11 | 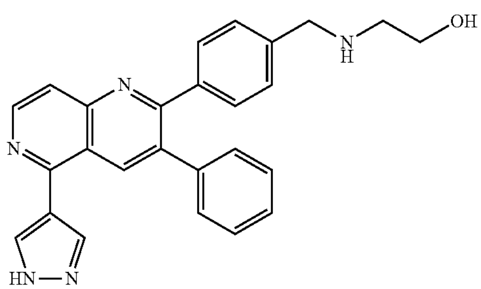 | 2-({4-[3-phenyl-5-(1H-pyrazol-4-yl)-1,6-naphthyridin-2-Yl]benzyl}amino)ethanol | 422.5128 | 422.5117 |
| 1-12 | 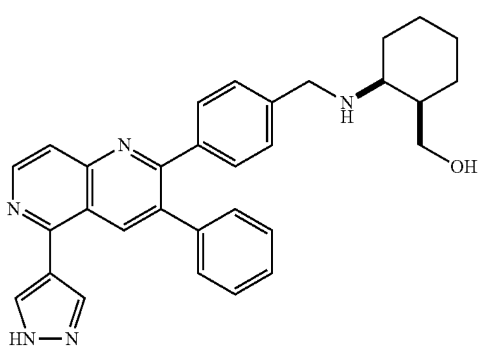 | [(1R,2S)-2-({4-[3-phenyl-5-(1H-pyrazol-4-yl)-1,6-naphthyridin-2-yl]benzyl}amino)cyclohexyl]methanol | 490.6325 | 490.6338 |
| 1-13 | 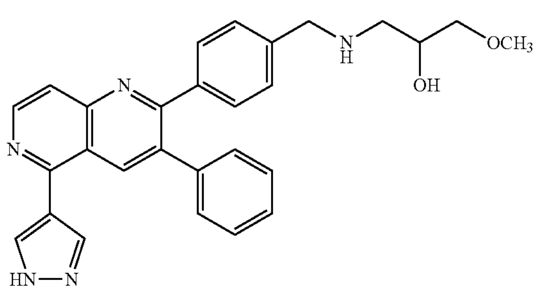 | (2S)-1-methoxy-3-({4-[3-phenyl-5-(1H-pyrazol-4-yl)-1,6-naphthyridin-2-yl]benzyl}amino)propan-2-ol | 466.5619 | 466.5685 |

TABLE 1-continued

| Cmp | Structure | Name | MS m/z (M + H): calc'd | MS m/z (M + H): observed |
|---|---|---|---|---|
| 1-14 | 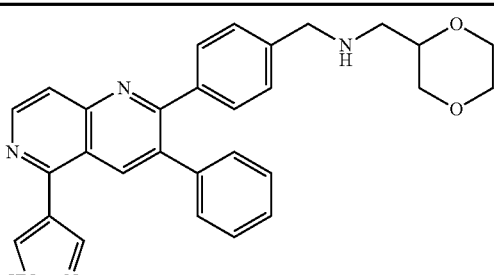 | 1-[(2S)-1,4-dioxan-2-yl]-N-{4-[3-phenyl-5-(1H-pyrazol-4-yl)-1,6-naphthyridin-2-yl]benzyl}methanamine | 478.5770 | 478.5759 |
| 1-15 | 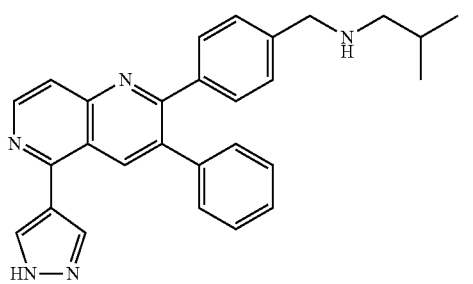 | 2-methyl-N-{4-[3-phenyl-5-(1H-pyrazol-4-yl)-1,6-naphthyridin-2-yl]benzyl}propan-1-amine | 434.5660 | 434.5639 |
| 1-16 | 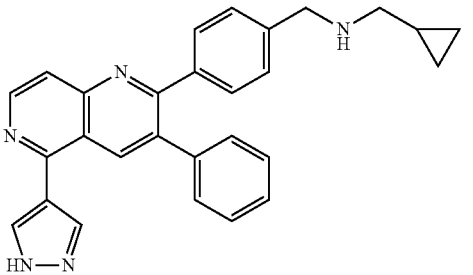 | 1-cyclopropyl-N-{4-[3-phenyl-5-(1H-pyrazol-4-yl)-1,6-naphthyridin-2-yl]benzyl}methanamine | 432.5487 | 432.5484 |
| 1-17 | 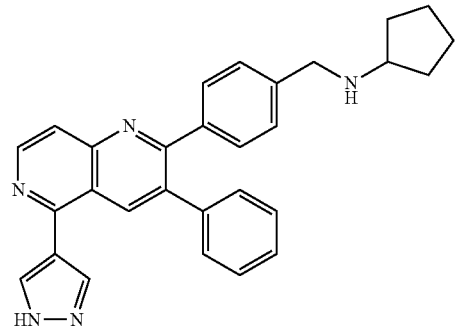 | N-{4-[3-phenyl-5-(1H-pyrazol-4-yl)-1,6-naphthyridin-2-yl]benzyl}cyclopentanamine | 456.5701 | 456.5783 |
| 1-18 | 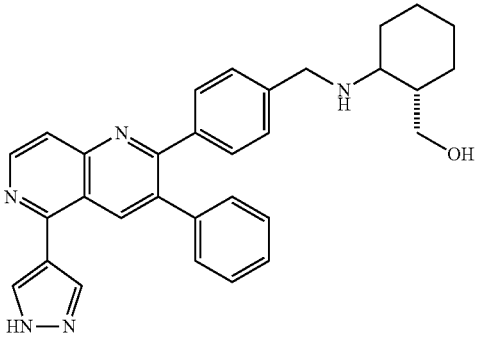 | [(1S,2R)-2-({4-[3-phenyl-5-(1H-pyrazol-4-yl)-1,6-naphthyridin-2-yl]benzyl}amino)cyclohexyl]methanol | 490.6329 | 490.6328 |

TABLE 1-continued

| Cmp | Structure | Name | MS m/z (M + H): calc'd | MS m/z (M + H): observed |
|---|---|---|---|---|
| 1-19 | 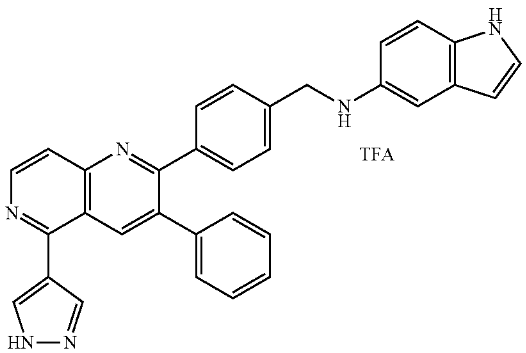 | N-{4-[3-phenyl-5-(1H-pyrazol-4-yl)-1,6-naphthyridin-2-yl]benzyl}-1H-indol-5-aminium trifluoroacetate | 493.5977 | 493.5958 |
| 1-20 | 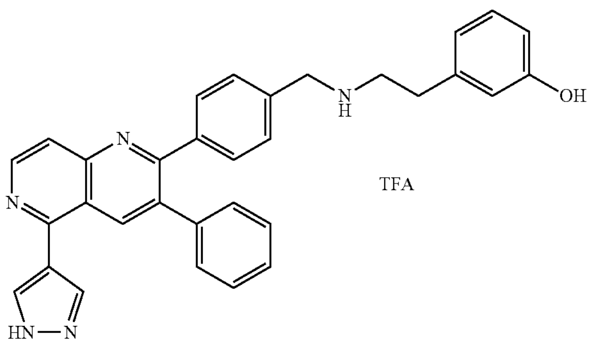 | 2-(3-hydroxyphenyl)-N-{4-[3-phenyl-5-(1H-pyrazol-4-yl)-1,6-naphthyridin-2-yl]benzyl}ethanaminium trifluoroacetate | 498.2279 | 498.2284 |
| 1-21 | 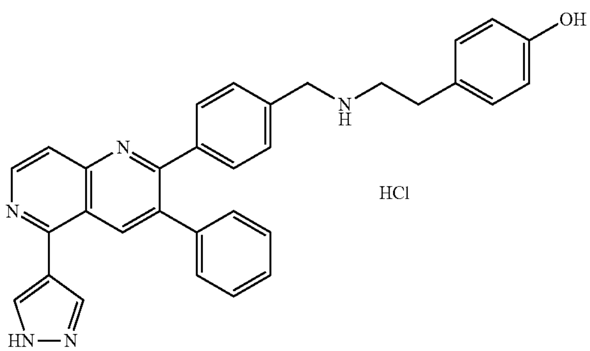 | 2-(4-hydroxyphenyl)-N-{4-[3-phenyl-5-(1H-pyrazol-4-yl)-1,6-naphthyridin-2-yl]benzyl}ethanaminium chloride | 498.2279 | 498.2224 |
| 1-22 | 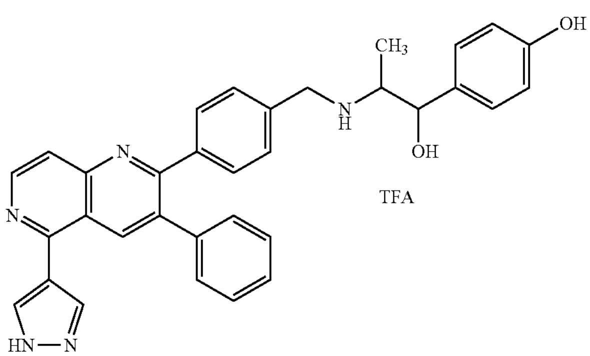 | 1-hydroxy-1-(4-hydroxyphenyl)-N-{4-[3-phenyl-5-(1H-pyrazol-4-yl)-1,6-naphthyridin-2-yl]benzyl}propan-2-aminium trifluoroacetate | 528.6281 | 528.6284 |

TABLE 1-continued
| Cmp | Structure | Name | MS m/z (M + H): calc'd | MS m/z (M + H): observed |
|---|---|---|---|---|
| 1-23 | 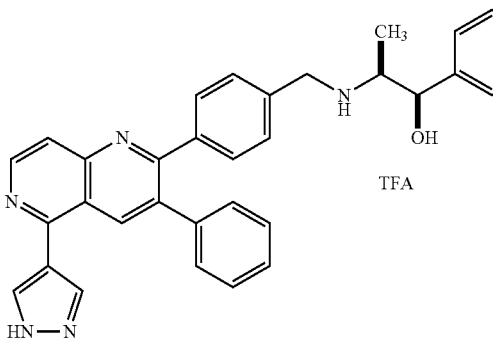 | (1R,2S)-1-hydroxy-1-(4-hydroxyphenyl)-N-{4-[3-phenyl-5-(1H-pyrazol-4-yl)-1,6-naphthyridin-2-yl]benzyl}propan-2-aminium trifluoroacetate | 528.6281 | 528.6281 |
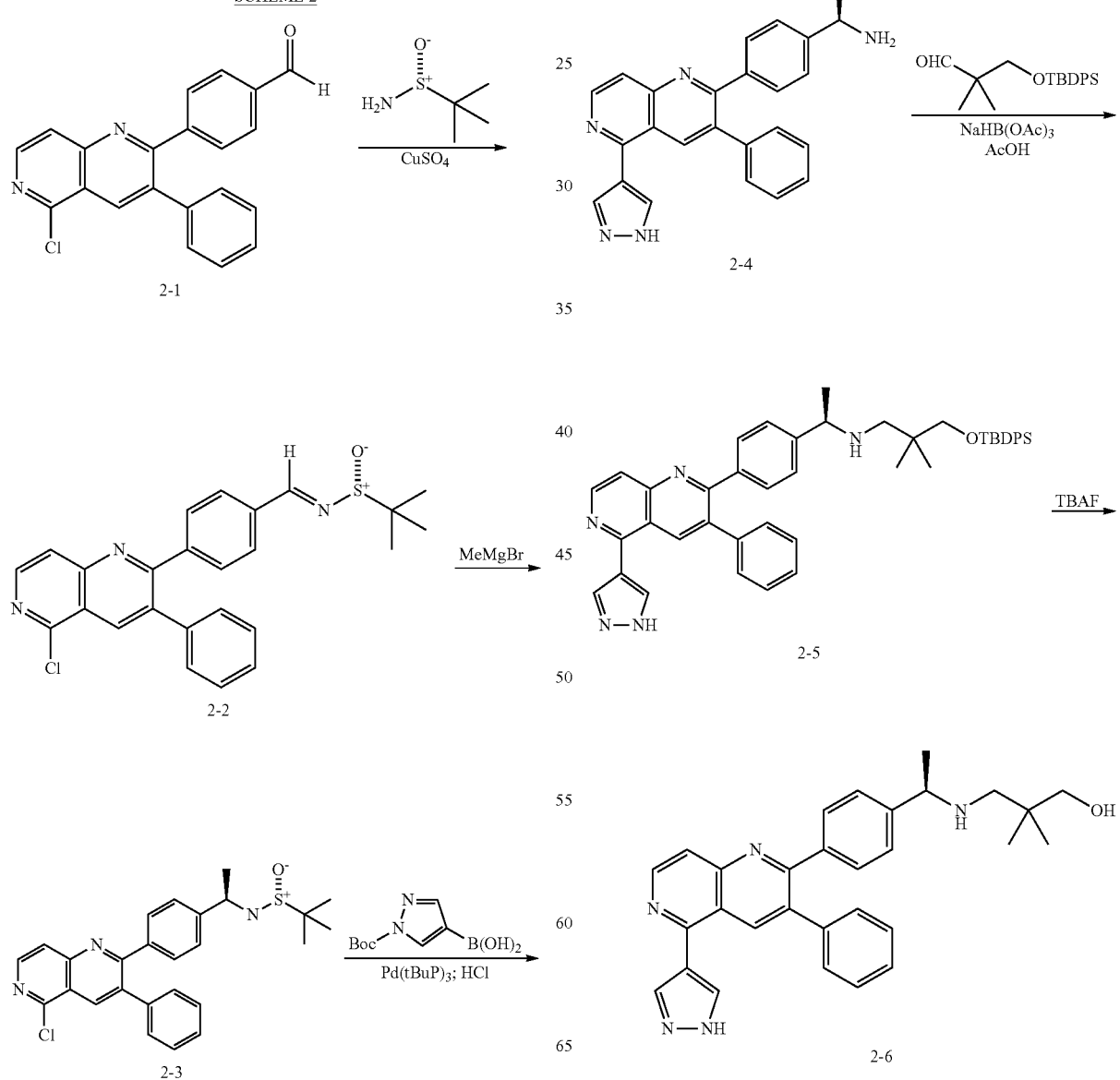

(2,2-dimethyl-3-{[(1R)-1-{4-[3-phenyl-5-(1H-pyra-zol-4-yl)-1,6-naphthyridin-2-yl]phenyl}ethyl]amino}propan-1-ol (2-6)

tert-butyl({(E)-[4-(5-chloro-3-phenyl-1,6-naphthyri-din-2-yl)phenyl]methylidene}amino)sulfoniumolate (2-2)

(S-(−)-2-methyl-2-propane-sulfinamide (13 g, 110 mmol), cupric sulfate (17 g, 95 mmol) and 4-(5-chloro-3-phenyl-1,6-naphthyridin-2-yl)benzaldehyde (2-1, 17 g, 50 mmol, Reference: WO2006135627A2, Dec. 21, 2006) were stirred under nitrogen in methylene chloride (100 mL) at 40° C. for 48 hours. The reaction mixture was cooled, filtered through celite, rinsed with methylene chloride, concentrated, and purified by silica gel chromatography (0-45% EtOAc in hexane with 5% DCM) to give tert-butyl({(E)-[4-(5-chloro-3-phenyl-1,6-naphthyridin-2-yl)phenyl]methylidene}amino)sulfoniumolate (2-2) as a pale'yellow foam. MS (M+H)$^+$: 448.4

N-{1-[4-(5-chloro-3-phenyl-1,6-naphthyridin-2-yl)phenyl]ethyl}-2-methylpropane-2-sulfinamide (2-3)

To a cooled (−10° C.) solution of 2-2 (1.0 g, 2.2 mmol) in methylene chloride (10 mL) was added methylmagnesium bromide (6.5 mL, 9.1 mmol, 1.4M in 75:25 toluene:THF) dropwise. The reaction mixture was maintained at −10° C. for 2 h before quenching with saturated ammonium chloride solution and stirring overnight at rt. The resulting mixture was extracted with methylene chloride, washed with brine, dried over magnesium sulfate, filtered, concentrated, and purified by silica gel chromatography (0-5% MeOH in DCM) to give an off-white foam as 10:1 mixture of diastereomers. The diastereomers were separated by reverse phase HPLC to give N-{1-[4-(5-chloro-3-phenyl-1,6-naphthyridin-2-yl)phenyl]ethyl}-2-methylpropane-2-sulfinamide (2-3) as a white solid as the major isomer. MS (M+H)$^+$: 464.4

(1R)-1-{4-[3-phenyl-5-(1H-pyrazol-4-yl)-1,6-naph-thyridin-2-yl]phenyl}ethanamine (2-4)

A solution of N-{1-[4-(5-chloro-3-phenyl-1,6-naphthyridin-2-yl)phenyl]ethyl}-2-methylpropane-2-sulfinamide (2-3, 0.10 g, 0.22 mmol), tert-butyl 4-(4,4,5,5-tetramethyl-1,3,2-dioxaborolan-2-yl)-1H-pyrazole-1-carboxylate (0.12 g, 0.39 mmol), cesium carbonate (0.21 g, 0.64 mmol) and bis(tri-t-butylphosphine)palladium(0) (0.013 g, 0.025 mmol) in a 7/3/1 mixture of dioxane/ethanol/water (3 mL) was heated to 100° C. in a microwave for 10 minutes. The crude reaction mixture was treated with HCl in ether (3 mL). After 30 minutes, the reaction was concentrated and purified by reverse phase chromatography (5-95% acetonitrile/water/0.1% TFA, Sunfire C18) to give (1R)-1-{4-[3-phenyl-5-(1H-pyrazol-4-yl)-1,6-naphthyridin-2-yl]phenyl}ethanamine (2-4) as a white solid. MS (M+H)$^+$: 428

3-{[tert-butyl(diphenyl)silyl]oxy}-2,2-dimethyl-N-[(1R)-1-{4-[3-phenyl-5-(1H-pyrazol-4-yl)-1,6-naph-thyridin-2-yl]phenyl}ethyl]propan-1-amine (2-5)

To a solution of (1R)-1-{4-[3-phenyl-5-(1H-pyrazol-4-yl)-1,6-naphthyridin-2-yl]phenyl}ethanamine (2-4, 0.030 g, 0.070 mmol) in dichloroethane (0.5 mL) and NMP (0.5 mL) was added diisopropylethylamine (0.024 mL, 0.14 mmol), 3-amino-2,2-dimethylpropan-1-ol (0.036 g, 0.11 mmol, Reference: Sugiyama, H.; Yokokawa, F.; Shioiri, T. *Tetrahedron,* 2003, 59(34), 6579-6593)) and acetic acid (0.010 mL, 0.17 mmol). After stirring at room temperature for 30 minutes, sodium triacetoxyborohydride (0.038 g, 0.18 mmol) was added and the reaction was stirred at room temperature for 15 hours. The reaction was poured into ethyl acetate, washed with 1M sodium hydroxide, water and brine. The organic layer was dried over sodium sulfate, filtered and concentrated under vacuum to give 3-{[tert-butyl(diphenyl)silyl]oxy}-2,2-dimethyl-N-[(1R)-1-{4-[3-phenyl-5-(1H-pyrazol-4-yl)-1,6-naphthyridin-2-yl]phenyl}ethyl]propan-1-amine (2-5) as an oil. MS (M+H)$^+$: calculated 716.0; found 716.4

(2,2-dimethyl-3-{[(1R)-1-{4-[3-phenyl-5-(1H-pyra-zol-4-yl)-1,6-naphthyridin-2-yl]phenyl}ethyl]amino}propan-1-ol (2-6)

To a solution of 3-{[teri-butyl(diphenyl)silyl]oxy}-2,2-dimethyl-N-[(1R)-1-{4-[3-phenyl-5-(1H-pyrazol-4-yl)-1,6-naphthyridin-2-yl]phenyl}ethyl]propan-1-amine (2-5, 0.050 g, 0.070 mmol) in THF (1.0 mL) was added 1M tetrabutylammonium fluoride in THF (0.70 mL, 0.70 mmol) at room temperature and the reaction was stirred at room temperature for 15 hours. The reaction was poured into ethyl acetate, washed with water and brine. The organic layer was dried over sodium sulfate, filtered and concentrated under vacuum. Purification by reverse phase chromatography (5-95% acetonitrile/water/0.1% TFA; Water Sunfire C18) gave (2,2-dimethyl-3-{[(1R)-1-{4-[3-phenyl-5-(1H-pyrazol-4-yl)-1,6-naphthyridin-2-yl]phenyl}ethyl]amino}propan-1-ol (2-6) as a yellow solid. HRMS (M+H)$^+$: calculated 478.2602; found 478.2626.

Example 1

Cloning of the Human Akt Isoforms and ΔPH-Akt1

The pS2neo vector (deposited in the ATCC on Apr. 3, 2001 as ATCC PTA-3253) was prepared as follows: The pRmHA3 vector (prepared as described in *Nucl. Acid Res.* 16:1043-1061 (1988)) was cut with BglII and a 2734 bp fragment was isolated. The pUChsneo vector (prepared as described in *EMBO J.* 4:167-171 (1985)) was also cut with BglII and a 4029 bp band was isolated. These two isolated fragments were ligated together to generate a vector termed pS2neo-1. This plasmid contains a polylinker between a metallothionein promoter and an alcohol dehydrogenase poly A addition site. It also has a neo resistance gene driven by a heat shock promoter. The pS2neo-1 vector was cut with Psp5II and BsiWI. Two complementary oligonucleotides were synthesized and then annealed (CTGCGGCCGC (SEQ. ID. NO.: 1) and GTACGCGGCCGCAG (SEQ. ID. NO.: 2)). The cut pS2neo-1 and the annealed oligonucleotides were ligated together to generate a second vector, pS2neo. Added in this conversion was a NotI site to aid in the linearization prior to transfection into S2 cells.

Human Akt1 gene was amplified by PCR (Clontech) out of a human spleen cDNA (Clontech) using the 5' primer: 5'CGC-GAATTCAGATCTACCATGAGCGACGTGGCTATTGTG 3' (SEQ. ID. NO.: 3), and the 3' primer: 5'CGCTCTAGAG-GATCCTCAGGCCGTGCTGCTGGC3' (SEQ. ID. NO.: 4). The 5' primer included an EcoRI and BglII site. The 3' primer included an XbaI and BamHI site for cloning purposes. The resultant PCR product was subcloned into pGEM3Z (Promega) as an EcoRI/Xba I fragment. For expression/purification purposes, a middle T tag was added to the 5' end of the full length Akt1 gene using the PCR primer: 5'GTACGAT-GCTGAACGATATCTTCG 3' (SEQ. ID. NO.: 5). The resulting PCR product encompassed a 5' KpnI site and a 3' BamHI site which were used to subclone the fragment in frame with a biotin tag containing insect cell expression vector, pS2neo.

For the expression of a pleckstrin homology domain (PH) deleted (Δaa 4-129, which includes deletion of a portion of the Akt1 hinge region) version of Akt1, PCR deletion mutagenesis was done using the full length Akt1 gene in the pS2neo vector as template. The PCR was carried out in 2 steps using overlapping internal primers (5'GAATACATGC-CGATGGAAAGCGACGGGGCTGAA-GAGATGGAGGTG 3' (SEQ. ID. NO.: 6), and 5'CCCCTC-CATCTCTTCAGCCCCGTCGCTTTCCATCGGCATG TATTC 3' (SEQ. ID. NO.: 7)) which encompassed the deletion and 5' and 3' flanking primers which encompassed the KpnI site and middle T tag on the 5' end. The final PCR product was digested with KpnI and SmaI and ligated into the pS2neo full length Akt1 KpnI/SmaI cut vector, effectively replacing the 5' end of the clone with the deleted version.

Human Akt3 gene was amplified by PCR of adult brain cDNA (Clontech) using the amino terminal oligo primer: 5' GAATTCAGATCTACCATGAGCGATGTTACCATTGTG 3' (SEQ. ID. NO.: 8); and the carboxy terminal oligo primer: 5' TCTAGATCTTATTCTCGTCCACTTGCAGAG 3'(SEQ. ID. NO.: 9).

These primers included a 5' EcoRI/BglII site and a 3' XbaI/BglII site for cloning purposes. The resultant PCR product was cloned into the EcoRI and XbaI sites of pGEM4Z (Promega). For expression/purification purposes, a middle T tag was added to the 5' end of the full length Akt3 clone using the PCR primer: 5'GGTACCATGGAATACATGCCGATG-GAAAGCGATGTTACCATTGTGAAG 3'(SEQ. ID. NO.: 10). The resultant PCR product encompassed a 5' KpnI site which allowed in frame cloning with the biotin tag containing insect cell expression vector, pS2neo.

Human Akt2 gene was amplified by PCR from human thymus cDNA (Clontech) using the amino terminal oligo primer: 5' AAGCTTAGATCTACCATGAATGAGGT-GTCTGTC 3' (SEQ. ID. NO.: 11); and the carboxy terminal oligo primer: 5'GAATTCGGATCCTCACTCGCGGAT-GCTGGC 3' (SEQ. ID. NO.: 12). These primers included a 5' HindIII/BglII site and a 3' EcoRI/BamHI site for cloning purposes. The resultant PCR product was subcloned into the HindIII/EcoRI sites of pGem3Z (Promega). For expression/purification purposes, a middle T tag was added to the 5' end of the full length Akt2 using the PCR primer: 5'GGTAC-CATGGAATACATGCCGATGGAAAATGAG-GTGTCTGTCATCAAAG 3' (SEQ. ID. NO.: 13). The resultant PCR product was subcloned into the pS2neo vector as described above.

Example 2

Expression of Human Akt Isoforms and ΔPH-Akt1

The DNA containing the cloned Akt1, Akt2, Akt3 and ΔPH-Akt1 genes in the pS2neo expression vector was purified and used to transfect Drosophila S2 cells (ATCC) by the calcium phosphate method. Pools of antibiotic (G418, 500 μg/ml) resistant cells were selected. Cell were expanded to a 1.0 L volume (~7.0×10⁶/ml), biotin and $CuSO_4$ were added to a final concentration of 50 μM and 50 mM respectively. Cells were grown for 72 h at 27° C. and harvested by centrifugation. The cell paste was frozen at −70° C. until needed.

Example 3

Purification of Human Akt Isoforms and ΔPH-Akt1

Cell paste from one liter of S2 cells, described in Example 2, was lysed by sonication with 50 mls 1% CHAPS in buffer A: (50 mM Tris pH 7.4, 1 mM EDTA, 1 mM EGTA, 0.2 mM AEBSF, 10 μg/ml benzamidine, 5 μg/ml of leupeptin, aprotinin and pepstatin each, 10% glycerol and 1 mM DTT). The soluble fraction was purified on a Protein G Sepharose fast flow (Pharmacia) column loaded with 9 mg/ml anti-middle T monoclonal antibody and eluted with 75 μM EYMPME (SEQ. ID. NO.: 14) peptide in buffer A containing 25% glycerol. Akt/PKB containing fractions were pooled and the protein purity evaluated by SDS-PAGE. The purified protein was quantitated using a standard Bradford protocol. Purified protein was flash frozen on liquid nitrogen and stored at −70° C.

Akt and Akt pleckstrin homology domain deletions purified from S2 cells required activation. Akt and Akt pleckstrin homology domain deletions were activated (Alessi et al. *Current Biology* 7:261-269) in a reaction containing 10 nM PDK1 (Upstate Biotechnology, Inc.), lipid vesicles (10 μM phosphatidylinositol-3,4,5-trisphosphate—Metreya, Inc, 100 μM phosphatidylcholine and 100 μM phosphatidylserine—Avanti Polar lipids, Inc.) and activation buffer (50 mM Tris pH7.4, 1.0 mM DTT, 0.1 mM EGTA, 1.0 μM Microcystin—LR, 0.1 mM ATP, 10 mM $MgCl_2$, 333 μg/ml BSA and 0.1 mM EDTA). The reaction was incubated at 22° C. for 4 hours. Aliquots were flash frozen in liquid nitrogen.

Example 4

Akt Kinase Assays

Activated Akt isoforms and pleckstrin homology domain deletion constructs were assayed utilizing a GSK-derived biotinylated peptide substrate. The extent of peptide phosphorylation was determined by Homogeneous Time Resolved Fluorescence (HTRF) using a lanthanide chelate (Lance)-coupled monoclonal antibody specific for the phosphopeptide in combination with a streptavidin-linked allophycocyanin (SA-APC) fluorophore which will bind to the biotin moiety on the peptide. When the Lance and APC are in proximity (i.e. bound to the same phosphopeptide molecule), a non-radiative energy transfer takes place from the Lance to the APC, followed by emission of light from APC at 665 nm.

Materials Required for the Assay:

A. Activated Akt isozyme or pleckstrin homology domain deleted construct
B. Akt peptide substrate: GSK3α (S21) Peptide #3928 biotin-GGRARTSSFAEPG (SEQ. ID. NO.:15), Macromolecular Resources.
C. Lance labeled anti-phospho GSK3α monoclonal antibody (Cell Signaling Technology, clone #27).
D. SA-APC (Prozyme catalog no. PJ25S lot #896067).
E. Microfluor® B U Bottom Microtiter Plates (Dynex Technologies, Catalog no. 7205).
F. Discovery® HTRF Microplate Analyzer, Packard Instrument Company.
G. 100× Protease Inhibitor Cocktail (PIC): 1 mg/ml benzamidine, 0.5 mg/ml pepstatin, 0.5 mg/ml leupeptin, 0.5 mg/ml aprotinin.
H. 10×Assay Buffer: 500 mM HEPES, pH 7.5, 1% PEG, mM EDTA, 1 mM EGTA, 1% BSA, 20 mM θ-Glycerol phosphate.
I. Quench Buffer: 50 mM HEPES pH 7.3, 16.6 mM EDTA, 0.1% BSA, 0.1% Triton X-100, 0.17 nM Lance labeled monoclonal antibody clone #27, 0.0067 mg/ml SA-APC
J. ATP/$MgCl_2$ working solution: 1×Assay buffer, 1 mM DTT, 1×PIC, 125 mM KCl, 5% Glycerol, 25 mM $MgCl_2$, 375 TM ATP K. Enzyme working solution: 1× Assay buffer, 1 mM DTT, 1×PIC, 5% Glycerol, active Akt. The final enzyme concentrations were selected so that the assay was in a linear response range.

L. Peptide working solution: 1× Assay buffer, 1 mM DTT, 1×PIC, 5% Glycerol, 2 TM GSK3 biotinylated peptide #3928

The reaction is assembled by adding 16 Tl of the ATP/MgCl$_2$ working solution to the appropriate wells of a 96-well microtiter plate. Inhibitor or vehicle (1.0 Tl) is added followed by 10 Tl of peptide working solution. The reaction is started by adding 13 Tl of the enzyme working solution and mixing. The reaction is allowed to proceed for 50 mM and then stopped by the addition of 60 Tl HTRF quench buffer. The stopped reactions were incubated at room temperature for at least 30 min and then read on the Discovery instrument.

Procedure for Streptavidin Flash Plate Assay:
Step 1:
A 1 µl solution of the test compound in 100% DMSO was added to 20 µl of 2× substrate solution (20 uM GSK3 Peptide, 300 µM ATP, 20 mM MgCl$_2$, 20 µCi/ml [γ$^{33}$P]ATP, 1× Assay Buffer, 5% glycerol, 1 mM DTT, 1×PIC, 0.1% BSA and 100 mM KCl). Phosphorylation reactions were initiated by adding 19 µl of 2× Enzyme solution (6.4 nM active Akt/PKB, 1× Assay Buffer, 5% glycerol, 1 mM DTT, 1×PIC and 0.1% BSA). The reactions were then incubated at room temperature for 45 minutes.
Step 2:
The reaction was stopped by adding 170 µl of 125 mM EDTA. 200 µl of stopped reaction was transferred to a Streptavidin Flashplate® PLUS (NEN Life Sciences, catalog no. SMP103). The plate was incubated for ≧10 minutes at room temperature on a plate shaker. The contents of each well was aspirated, and the wells rinsed 2 times with 200 µl TBS per well. The wells were then washed 3 times for 5 minutes with 200 µl TBS per well with the plates incubated at room temperature on a platform shaker during wash steps.

The plates were covered with sealing tape and counted using the Packard TopCount with the appropriate settings for counting [$^{33}$P] in Flashplates.

Procedure for Streptavidin Filter Plate Assay:
Step 1:
The enzymatic reactions as described in Step 1 of the Streptavidin Flash Plate Assay above were performed.
Step 2:
The reaction was stopped by adding 20 µl of 7.5M Guanidine Hydrochloride. 50 µl of the stopped reaction was transferred to the Streptavidin filter plate (SAM$^{2TM}$ Biotin Capture Plate, Promega, catalog no. V7542) and the reaction was incubated on the filter for 1-2 minutes before applying vacuum.

The plate was then washed using a vacuum manifold as follows: 1) 4×200 µl/well of 2M NaCl; 2) 6×200 µl/well of 2M NaCl with 1% H$_3$PO$_4$; 3) 2×200 µl/well of diH$_2$0; and 4) 2×100 µl/well of 95% Ethanol. The membranes were then allowed to air dry completely before adding scintillant.

The bottom of the plate was sealed with white backing tape, 30 µl/well of Microscint 20 (Packard Instruments, catalog no. 6013621) was added. The top of the plate was sealed with clear sealing tape, and the plate then counted using the Packard TopCount with the appropriate settings for [$^{33}$P] with liquid scintillant.

Procedure for Phosphocellulose Filter Plate Assay:
Step 1:
The enzymatic reactions were performed as described in Step 1 of the Streptavidin Flash Plate Assay (above) utilizing KKGGRARTSSFAEPG (SEQ. ID. NO.: 16) as the substrate in place of biotin-GGRARTSSFAEPG.

Step 2:
The reaction was stopped by adding 20 µl of 0.75% H$_3$PO$_4$. 50 µl of stopped reaction was transferred to the filter plate (UNIFILTER™, Whatman P81 Strong Cation Exchanger, White Polystyrene 96 Well Plates, Polyfiltronics, catalog no. 7700-3312) and the reaction incubated on the filter for 1-2 minutes before applying vacuum.

The plate was then washed using a vacuum manifold as follows: 1) 9×200 µl/well of 0.75% H$_3$PO$_4$; and 2) 2×200 µl/well of diH$_2$0. The bottom of the plate was sealed with white backing tape, then 30 µl/well of Microscint 20 was added. The top of the plate was sealed with clear sealing tape, and the plate counted using the Packard TopCount with the appropriate settings for [$^{33}$P] and liquid scintillant.

PKA Assay:
Each individual PKA assay consists of the following components:
A. 5×PKA assay buffer (200 mM Tris pH7.5, 100 mM MgCl$_2$, 5 mM θ-mercaptoethanol, 0.5 mM EDTA)
B. 50 µM stock of Kemptide (Sigma) diluted in water
C. $^{33}$P-ATP prepared by diluting 1.0 µl $^{33}$P-ATP [10 mCi/ml] into 200 Tl of a 50 µM stock of unlabeled ATP
D. 10 µl of a 70 nM stock of PKA catalytic subunit (UBI catalog #14-114) diluted in 0.5 mg/ml BSA
E. PKA/Kemptide working solution: equal volumes of 5×PKA assay buffer, Kemptide solution and PKA catalytic subunit.

The reaction is assembled in a 96 deep-well assay plate. The inhibitor or vehicle (10 Tl) is added to 10 Tl of the $^{33}$P-ATP solution. The reaction is initiated by adding 30 Tl of the PKA/Kemptide working solution to each well. The reactions were mixed and incubated at room temperature for 20 min. The reactions were stopped by adding 50 Tl of 100 mM EDTA and 100 mM sodium pyrophosphate and mixing.

The enzyme reaction product (phosphorylated Kemptide) was collected on p81 phosphocellulose 96 well filter plates (Millipore). To prepare the plate, each well of a p81 filter plate was filled with 75 mM phosphoric acid. The wells were emptied through the filter by applying a vacuum to the bottom of the plate. Phosphoric acid (75 mM, 170 µl) was added to each well. A 30 µl aliquot from each stopped PKA reaction was added to corresponding wells on the filter plate containing the phosphoric acid. The peptide was trapped on the filter following the application of a vacuum and the filters were washed 5 times with 75 mM phosphoric acid. After the final wash, the filters were allowed to air dry. Scintillation fluid (30 µl) was added to each well and the filters counted on a TopCount (Packard).

PKC Assay:
Each PKC assay consists of the following components:
A. 10×PKC co-activation buffer: 2.5 mM EGTA, 4 mM CaCl$_2$
B. 5×PKC activation buffer: 1.6 mg/ml phosphatidylserine, 0.16 mg/ml diacylglycerol, 100 mM Tris pH 7.5, 50 mM MgCl$_2$, 5 mM θ-mercaptoethanol
C. $^{33}$P-ATP prepared by diluting 1.0 µl $^{33}$P-ATP [10 mCi/ml] into 100 µl of a 100 µM stock of unlabeled ATP
D. Myelin basic protein (350 µg/ml, UBI) diluted in water
E. PKC (50 ng/ml, UBI catalog #14-115) diluted into 0.5 mg/ml BSA
F. PKC/Myelin Basic Protein working solution: Prepared by mixing 5 volumes each of PKC co-activation buffer and Myelin Basic protein with 10 volumes each of PKC activation buffer and PKC.

The assays were assembled in 96 deep-well assay plates. Inhibitor or vehicle (10 Tl) was added to 5.0 ul of $^{33}$P-ATP. Reactions were initiated with the addition of the PKC/Myelin Basic Protein working solution and mixing. Reactions were incubated at 30° C. for 20 min. The reactions were stopped by adding 50 Tl of 100 mM EDTA and 100 mM sodium pyrophosphate and mixing. Phosphorylated Mylein Basic Protein was collected on PVDF membranes in 96 well filter plates and quantitated by scintillation counting.

Compounds of the instant invention described in the Schemes and Tables were tested in the assay described above and were found to have $IC_{50}$ of $\leq 50$ µM against one or more of Akt1, Akt2 and Akt3.

Example 5

Cell Based Assays to Determine Inhibition of Akt/PKB

Cells (for example LnCaP or a $PTEN^{(-/-)}$ tumor cell line with activated Akt/PKB) were plated in 100 mM dishes. When the cells were approximately 70 to 80% confluent, the cells were refed with 5 mls of fresh media and the test compound added in solution. Controls included untreated cells, vehicle treated cells and cells treated with either LY294002 (Sigma) or wortmanin (Sigma) at 20 µM or 200 nM, respectively. The cells were incubated for 2, 4 or 6 hrs, and the media removed, the cells were washed with PBS, scraped and transferred to a centrifuge tube. They were pelleted and washed again with PBS. Finally, the cell pellet was resuspended in lysis buffer (20 mM Tris pH8, 140 mM NaCl, 2 mM EDTA, 1% Triton, 1 mM Na Pyrophosphate, 10 mM θ-Glycerol Phosphate, 10 mM NaF, 0.5 mm $NaVO_4$, 1 µM Microsystine, and 1× Protease Inhibitor Cocktail), placed on ice for 15 minutes and gently vortexed to lyse the cells. The lysate was spun in a Beckman tabletop ultra centrifuge at 100,000×g at 4° C. for 20 min. The supernatant protein was quantitated by a standard Bradford protocol (BioRad) and stored at –70° C. until needed.

Proteins were immunoprecipitated (IP) from cleared lysates as follows: For Akt1/PKBI, lysates are mixed with Santa Cruz sc-7126 (D-17) in NETN (100 mM NaCl, 20 mM Tris pH 8.0, 1 mM EDTA, 0.5% NP-40) and Protein A/G Agarose (Santa Cruz sc-2003) was added. For Akt2/PKBθ, lysates were mixed in NETN with anti-Akt2 agarose (Upstate Biotechnology #16-174) and for Akt3/PKBK, lysates were mixed in NETN with anti-Akt3 agarose (Upstate Biotechnology #16-175). The IPs were incubated overnight at 4° C., washed and seperated by SDS-PAGE.

Western blots were used to analyze total Akt, pThr308 Akt1, pSer473 Akt1, and corresponding phosphorylation sites on Akt2 and Akt3, and downstream targets of Akt using specific antibodies (Cell Signaling Technology): Anti-Total Akt (cat. no. 9272), Anti-Phopho Akt Serine 473 (cat. no. 9271), and Anti-Phospho Akt Threonine 308 (cat. no. 9275). After incubating with the appropriate primary antibody diluted in PBS+0.5% non-fat dry milk (NFDM) at 4° C. overnight, blots were washed, incubated with Horseradish peroxidase (HRP)-tagged secondary antibody in PBS+0.5% NFDM for 1 hour at room temperature. Proteins were detected with ECL Reagents (Amersham/Pharmacia Biotech RPN2134).

Example 6

Heregulin Stimulated Akt Activation

MCF7 cells (a human breast cancer line that is $PTEN^{+/+}$) were plated at $1\times10^6$ cells per 100 mM plate. When the cells were 70-80% confluent, they were referred with 5 ml of serum free media and incubated overnight. The following morning, compound was added and the cells were incubated for 1-2 hrs, after which time heregulin was added (to induce the activation of Akt) for 30 minutes and the cells were analyzed as described above.

Example 7

Inhibition of Tumor Growth

In vivo efficacy of an inhibitor of the growth of cancer cells may be confirmed by several protocols well known in the art.

Human tumor cell lines which exhibit a deregulation of the PI3K pathway (such as LnCaP, PC3, C33a, OVCAR-3, MDA-MB-468, A2780 or the like) are injected subcutaneously into the left flank of 6-10 week old female nude (also male mice [age 10-14 weeks] are used for prostate tumor xenografts [LnCaP and PC3]) mice (Harlan) on day 0. The mice are randomly assigned to a vehicle, compound or combination treatment group. Daily subcutaneous administration begins on day 1 and continues for the duration of the experiment. Alternatively, the inhibitor test compound may be administered by a continuous infusion pump. Compound, compound combination or vehicle is delivered in a total volume of 0.2 ml. Tumors are excised and weighed when all of the vehicle-treated animals exhibited lesions of 0.5-1.0 cm in diameter, typically 4 to 5.5 weeks after the cells were injected. The average weight of the tumors in each treatment group for each cell line is calculated.

Example 8

Spot Multiplex Assay

This procedure describes a sandwich immunoassay used to detect multiple phosphorylated proteins in the same well of a 96 well format plate. Cell lysates are incubated in 96-well plates on which different capture antibodies are placed on spatially distinct spots in the same well. Phoshorylation-specific rabbit polyclonal antibodies are added and the complex is detected by an anti-rabbit antibody labeled with an electrochemiluminescent tag.

96-Well LNCaP Plates +/−Compounds:

Spin in Beckman J6 1200 rpm 10 min, aspirate media. Add 50 µl/well: TBS (Pierce #28376-20 mM Tris pH 7.5, 150 mM NaCl)+1% Triton X-100+Protease and Phosphatase Inhibitors. Wrap in plastic wrap, place in −70° C. freezer until completely frozen. Block Multiplex Plates (Meso Scale Discovery, Gaithersburg, Md.) with 3% Blocker A in 1× Tris Wash Buffer, 1500/well. Cover with plate sealer, incubate on Micromix shaker RT 2 h (minimum). Wash with 1×RCM 51 (TTBS). Thaw cell lysate plates on ice, add 40 µl lysate/well into blocked plates. Cover with plate sealer, incubate on Micromix shaker 4° C., O/N, Wash with 1×RCM 51. Dilute Secondary Antibodies in 1% Blocker A in 1× Tris Wash Buffer: Anti phospho AKT (T308), Anti phospho Tuberin (T1462), alone or in combination. Add 25 µl/well, cover with plate sealer, incubate on Micromix shaker RT 3 h. Wash with 1×RCM 51. Dilute Ru-GAR in 1% Blocker A in 1× Tris Wash Buffer. Add 25 µl/well, cover with plate sealer, incubate on Micromix shaker RT 1 h. Wash with 1×RCM 51. Dilute 4× Read Buffer T to 1× with Water, add 200 µl diluted Read Buffer/well Read on Sector 6000 Imager.

Protease and Phosphatase Inhibitors:

Microcystin-LR, Calbiochem #475815 to 1 µM final concentration (stock=500 µM)

Calbiochem #524624, 100× Set I
Calbiochem #524625, 100× Set II
Calbiochem #539134, 100× Set III
Anti Phospho AKT (T308):
Cell Signaling Technologies #9275
Anti Phospho Tuberin (T1462):
Covance Affinity Purified (Rabbits MS 2731/2732)
Ru-GAR=Ruthenylated Goat anti Rabbit
10× Tris Wash Buffer, Blocker A and 4× Read Buffer T
10×RCM 51 (10×TTBS, RCM 51)
1×=20 mM Tris pH 7.5, 140 mM NaCl, 0.1% Tween-20

Example 9

Cell-Based (In-Vivo) Assay

This procedure describes a cell-based (in vivo) activity assay for the Akt serine/threonine kinase. Activated endogenous Akt is capable of phosphorylating a specific Akt substrate (GSK3β) peptide which is biotinylated. Detection is performed by Homogeneous Time Resolved Fluorescence (HTRF) using a Europium Kryptate [Eu(K)] coupled antibody specific for the phosphopeptide and streptavidin linked XL665 fluorophore which will bind to the biotin moiety on the peptide. When the [Eu(K)] and XL665 are in proximity (i.e. bound to the same phosphopeptide molecule) a non-radiative energy transfer takes place from the Eu(K) to the XL665, followed by emission of light from XL665 at 665 nm.

The assay can be used to detect inhibitors of all three Akt isozymes (Akt1, Akt2, and Akt3) from multiple different species if specific antibodies to each exist.

Materials and Reagents
A. Cell Culture Microtiter Flat Bottom 96 well plates, Corning Costar, Catalog no. 3598
B. Reacti-Bind Protein A Coated 96-well plates, Pierce, Catalog no 15130.
C. Reacti-Bind Protein G Coated 96-well plates, Pierce, Catalog no 15131.
D. Micromix 5 Shaker.
E. Microfluor®B U Bottom Microtiter Plates, Dynex Technologies, Catalog no. 7205.
F. 96 Well Plate Washer, Bio-Tek Instruments, Catalog no. EL 404.
G. Discovery® HTRF Microplate Analyzer, Packard Instrument Company.
Buffer Solutions
A. IP Kinase Cell Lysis Buffer: 1×TBS; 0.2% Tween 20; 1× Protease Inhibitor Cocktail III (Stock is 100×, Calbiochem, 539134); 1× Phosphatase Inhibitor Cocktail I (Stock is 100×, Calbiochem, 524624); and 1× Phosphatase Inhibitor Cocktail II (Stock is 100×, Calbiochem, 524625).
B. 10× Assay Buffer: 500 mM Hepes pH 7.5; 1% PEG; 1 mM EDTA; 1 mM EGTA; and 20 mM β-glycerophosphate.
C. IP Kinase Assay Buffer: 1× Assay Buffer; 50 mM KCl; 150 uM ATP; 10 mM $MgCl_2$; 5% Glycerol; 1 mM DTT; 1 Tablet Protease Inhibitor Cocktail per 50 ml Assay Buffer; and 0.1% BSA
D. GSK3β Substrate Solution: IP Kinase Assay Buffer; and 500 nM Biotinylated GSK3β peptide.
E. Lance Buffer: 50 mM Hepes pH 7.5; 0.1% BSA; and 0.1% Triton X-100.
F. Lance Stop Buffer: Lance Buffer; and 33.3 mM EDTA.
G. Lance Detection Buffer: Lance Buffer; 13.3 μg/ml SA-APC; and 0.665 nM EuK Ab a-phospho (Ser-21) GSK3β

Multi-Step Immunoprecipitation Akt Kinase Assay
Day 1
A. Seed C33a cells Step: Plate 60,000 C33a cells/well in 96 well microtiter plate.
B. Incubate cells overnight at 37° C.
Day 2
D. Compound Addition Step: Add compounds in fresh media (alpha-MEM/10% FBS, room temp) to 96 well plate from above and incubate for 5 hrs in tissue culture incubator.
E. Cell Lysis Step: Aspirate media and add 100 μl of IP Kinase Cell Lysis Buffer.
F. Freeze 96 well microtiter plate at −70° C. (NOTE: This step can be done for a minimum of 1 hour or overnight.)
Day 3
G. Coat Protein A/G 96 well plate Step: Add appropriate concentration of α-Akt antibody (Akt1, Akt2, or Akt3) in a 100 μl of PBS to the following wells:

α-Akt 1 (20 ng/well/100 ul) B2>>>>>>>B10/rows B-G/Akt1 plate

α-Akt 2 (50 ng/well/100 ul) B2>>>>>>>B10/rows B-G/Akt2 plate

Rabbit-IgG (150 ng/well/100 ul): B11-G11 on every plate (Akt1 and Akt2)

H. Incubate in the cold room (+4° C.) for 4 hours on the Micromix 5 (Form 20; Attitude 2) (NOTE: Attitude depends on which Micromix 5 machine).
I. Aspirate off α-Akt antibody solution and add 100 μl of PBS to each well.
J. Akt Immunoprecipitation Step: To the 100 μl of PBS from Step (I) add 5 μl of thawed cell lystate for Akt1 plates and 10 μl of thawed cell lysate for Akt2 plates. NOTE: Thaw cell lysate on ice. Mix thawed lysate by pipetting up & down 10× before transferring to antibody plates. Keep the cell lysate plates on ice. After transfer of cell lysate to the antibody plates refreeze the cell lysate plates at −70° C.
K. Incubate in the cold room (+4° C.) overnight on Micromix 5 shaker (form 20, attitude 3).
Day 4
L. Immunoprecipitation Plate Wash Step: Wash 96 well plates 1× with TTBS (RCM 51, 1×=2 cycles) using the 96-Well Plate Washer. Fill wells with TTBS and incubate for 10 minutes. Wash 96 well plates 2× with TTBS. (NOTE: Prime plate washer before use: 1. Check buffer reservoirs, making sure they are full and 2. empty waste containers.
M. Manual Plate Wash Step: Add 180 μl of IP Kinase Assay buffer.
N. Start Akt Enzyme Reaction: Aspirate supernatant. Add 60 μl of GSK30 Substrate Solution.
O. Incubate for 2.5 hours on Micromix 5 shaker @ RT. NOTE: Time of incubation should be adjusted so that the ratio of Column 10/Column 11 is not >10.
P. Combine 30 μl of Lance Detection Buffer with 30 μl of Lance Stop Buffer (60 μl total/well) and add to Microfluor U bottom 96 well black plates.
Q. Stop Akt Enzyme Reaction: Transfer 40 μl of Akt Enzyme Reaction Mix from Protein A/G 96 well plate from Step (O) to Microfluor U bottom 96 well black plates from Step (P).
U. Incubate at room temperature for 1-2 hrs on Micromix 5 shaker (form 20, attitude 3), then read with the Discovery HTRF Microplate Analyzer using Akt program.

| IP Kinase Cell Lysis Buffer 100 μl per well | | |
|---|---|---|
| | 8 ml (1 Plate) | 45 ml (6 Plates) |
| 1X TBS | 7744 μl | NA |
| Tween 20 | 20 μl | NA |
| 1X Protease Inhibitor Cocktail III | 80 μl | NA |
| 1X Phosphatase Inhibitor Cocktail I | 80 μl | 450 μl |
| 1X Phosphatase Inhibitor Cocktail II | 80 μl | 450 μl |
| Microcystin LR (500X) | | 90 μl |

| IP Kinase Assay Buffer 100 μl per well | | |
|---|---|---|
| | 8 ml (1 Plate) | 50 ml (3 Plates) |
| 10X Assay Buffer | 800 μl | 5 ml |
| 1M KCl | 400 μl | 2.5 ml |
| 250 mM ATP | 4.8 μl | 30 μl |
| 1M MgCl$_2$ | 80 μl | 500 μl |
| Glycerol | 400 μl | 2.5 ml |
| 1M DTT | 8 μl | 50 μl |
| Protease Inhibitor Cocktail | 1 tablet/50 ml | 1 |
| 10% BSA | 80 μl | 500 μl |
| di dH$_2$0 | 6227.2 μl | 38.9 ml |

| GSK3β Substrate Solution 60 μl per well | | |
|---|---|---|
| | 5 ml (1 Plate) | 7 ml |
| IP Kinase Assay Buffer | 5 ml | — |
| 1 mM GSK3β peptide | 2.5 μl | 3.5 μl |

| Lance Stop Buffer 30 μl per well | | |
|---|---|---|
| | 3 ml (1 Plate) | 5 ml | 5 ml |
| 1X Lance Buffer | 2800.2 μl | | |
| EDTA 0.5M | 199.8 μl | | |

| Lance Detection Buffer 30 μl per well | | |
|---|---|---|
| | 3 ml (1 Plate) | 5 ml |
| SA-APC (1 mg/ml in ddH2O, dilute 1/75.2 in Lance Buffer) | 40 μl | 66.7 μl |
| EuK Ab a-phospho (Ser 21)GSK3β (680 nM, dilute 1/1133 in Lance Buffer) | 2.7 μl | 4.5 μl |

What is claimed is:

1. A compound according to Formula A:

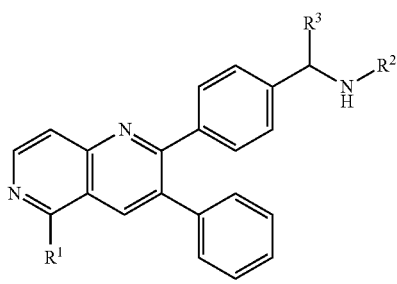

wherein:
- $R^1$ is aryl, heteroaryl or heterocyclyl;
- $R^2$ is a $(C_1-C_{10})$alkyl or heterocyclyl which are optionally substituted with from one to three substituents selected from OH, $O(C_1-C_6)$alkyl, phenyl and heterocyclyl, wherein said phenyl is optionally substituted with from one to three substituents selected from OH; and
- $R^3$ is a $(C_1-C_3)$alkyl or hydrogen;

or a pharmaceutically acceptable salt or a stereoisomer thereof.

2. A compound according to Formula A of claim 1, wherein:
- $R^1$ is aryl or heteroaryl;
- $R^2$ is a $(C_1-C_{10})$alkyl which is optionally substituted with from one to three substituents selected from OH, $O(C_1-C_6)$alkyl and phenyl, wherein said phenyl is optionally substituted with from one to three substituents selected from OH; and
- $R^3$ is methyl or hydrogen;

or a pharmaceutically acceptable salt or a stereoisomer thereof.

3. A compound according to Formula A of claim 1, wherein:
- $R^1$ is 4-pyrazolyl;
- $R^2$ is a $(C_1-C_{10})$alkyl or heterocyclyl which are optionally substituted with from one to three substituents selected from OH, $O(C_1-C_6)$alkyl, phenyl and heterocyclyl, wherein said phenyl is optionally substituted with from one to three substituents selected from OH; and
- $R^3$ is methyl or hydrogen;

or a pharmaceutically acceptable salt or a stereoisomer thereof.

4. A compound according to Formula A of claim 1, wherein:
- $R^1$ is 4-pyrazolyl;
- $R^2$ is a $(C_1-C_{10})$alkyl which is optionally substituted with from one to three substituents selected from OH, $O(C_1-C_6)$alkyl and phenyl, wherein said phenyl is optionally substituted with from one to three substituents selected from OH; and
- $R^3$ is methyl or hydrogen;

or a pharmaceutically acceptable salt or a stereoisomer thereof.

5. A compound according to Formula A of claim 1, wherein:
- $R^1$ is 4-pyrazolyl;
- $R^2$ is a $(C_1-C_{10})$alkyl which is optionally substituted with from one to three substituents selected from OH and $O(C_1-C_6)$alkyl; and
- $R^3$ is methyl or hydrogen;

or a pharmaceutically acceptable salt or a stereoisomer thereof.

6. A compound according to Formula A of claim 1, wherein:
- $R^1$ is 4-pyrazolyl;
- $R^2$ is a $(C_1-C_{10})$alkyl which is optionally substituted with from one to three substituents selected from OH and $OCH_3$; and
- $R^3$ is methyl or hydrogen;

or a pharmaceutically acceptable salt or a stereoisomer thereof.

7. A compound which is selected from:
- 2,2-dimethyl-3-({4-[3-phenyl-5-(1H-pyrazol-4-yl)-1,6-naphthyridin-2-yl]benzyl}amino) propan-1-ol;
- 3-({4-[3-phenyl-5-(1H-pyrazol-4-yl)-1,6-naphthyridin-2-yl]benzyl}amino)propan-1-ol;
- {1-[({4-[3-phenyl-5-(1H-pyrazol-4-yl)-1,6-naphthyridin-2-yl]benzyl}amino)methyl]cyclobutyl}methanol;
- {1-[({4-[3-phenyl-5-(1H-pyrazol-4-yl)-1,6-naphthyridin-2-yl]benzyl}amino)methyl]cyclopentyl}methanol;
- {1-[({4-[3-phenyl-5-(1H-pyrazol-4-yl)-1,6-naphthyridin-2-yl]benzyl}amino)methyl]cyclohexyl}methanol;
- 4-({4-[3-phenyl-5-(1H-pyrazol-4-yl)-1,6-naphthyridin-2-yl]benzyl}amino)butan-1-ol;
- 2,2-dimethyl-N-{4-[3-phenyl-5-(1H-pyrazol-4-yl)-1,6-naphthyridin-2-yl]benzyl}propan-1-amine;
- 2-({4-[3-phenyl-5-(1H-pyrazol-4-yl)-1,6-naphthyridin-2-yl]benzyl}amino)ethanol;
- [(1R,2S)-2-({4-[3-phenyl-5-(1H-pyrazol-4-yl)-1,6-naphthyridin-2-yl]benzyl}amino) cyclohexyl]methanol;
- (2S)-1-methoxy-3-({4-[3-phenyl-5-(1H-pyrazol-4-yl)-1,6-naphthyridin-2-yl]benzyl}amino)propan-2-ol;
- 1-[(2S)-1,4-dioxan-2-yl]-N-{4-[3-phenyl-5-(1H-pyrazol-4-yl)-1,6-naphthyridin-2-yl]benzyl}methanamine;
- 2-methyl-N-{4-[3-phenyl-5-(1H-pyrazol-4-yl)-1,6-naphthyridin-2-yl]benzyl}propan-1-amine;
- 1-cyclopropyl-N-{4-[3-phenyl-5-(1H-pyrazol-4-yl)-1,6-naphthyridin-2-yl]benzyl}methanamine;
- N-{4-[3-phenyl-5-(1H-pyrazol-4-yl)-1,6-naphthyridin-2-yl]benzyl}cyclopentanamine;
- [(1S,2R)-2-({4-[3-phenyl-5-(1H-pyrazol-4-yl)-1,6-naphthyridin-2-yl]benzyl}amino) cyclohexyl]methanol;

N-{4-[3-phenyl-5-(1H-pyrazol-4-yl)-1,6-naphthyridin-2-yl]benzyl}-1H-indol-5-amine;

3-[2-({4-[3-phenyl-5-(1H-pyrazol-4-yl)-1,6-naphthyridin-2-yl]benzyl}amino)ethyl]phenol;

4-[2-({4-[3-phenyl-5-(1H-pyrazol-4-yl)-1,6-naphthyridin-2-yl]benzyl}amino)ethyl]phenol;

4-[1-hydroxy-2-({4-[3-phenyl-5-(1H-pyrazol-4-yl)-1,6-naphthyridin-2-yl]benzyl}amino) propyl]phenol;

4-[(1R,2S)-1-hydroxy-2-({4-[3-phenyl-5-(1H-pyrazol-4-yl)-1,6-naphthyridin-2-yl]benzyl}amino)propyl]phenol; and (2,2-dimethyl-3-{[(1R)-1-{4-[3-phenyl-5-(1H-pyrazol-4-yl)-1,6-naphthyridin-2-yl]phenyl}ethyl]amino}propan-1-ol;

or a pharmaceutically acceptable salt or stereoisomer thereof.

8. A pharmaceutical composition comprising a pharmaceutical carrier, and dispersed therein, a therapeutically effective amount of a compound of claim 1.

* * * * *

SEQUENCE LISTING

```
<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: Completely Synthetic DNA Sequence

<400> SEQUENCE: 1
ctgcggccgc                                                             10

<210> SEQ ID NO 2
<211> LENGTH: 14
<212> TYPE: DNA
<213> ORGANISM: Artificial Sequence
<220> FEATURE:
<223> OTHER INFORMATION: Completely Synthetic DNA Sequence

<400> SEQUENCE: 2
gtacgcggcc gcag                                                        14

<210> SEQ ID NO 3
<211> LENGTH: 39
<212> TYPE: DNA
<213> ORGANISM: Artificial Sequence
<220> FEATURE:
<223> OTHER INFORMATION: Completely Synthetic DNA Sequence

<400> SEQUENCE: 3
```
cgcgaattca gatctaccat gagcgacgtg gctattgtg                    39

<210> SEQ ID NO 4
<211> LENGTH: 33
<212> TYPE: DNA
<213> ORGANISM: Artificial Sequence
<220> FEATURE:
<223> OTHER INFORMATION: Completely Synthetic DNA Sequence

<400> SEQUENCE: 4
cgctctagag gatcctcagg ccgtgctgct ggc                          33

<210> SEQ ID NO 5
<211> LENGTH: 24
<212> TYPE: DNA
<213> ORGANISM: Artificial Sequence
<220> FEATURE:
<223> OTHER INFORMATION: Completely Synthetic DNA Sequence

<400> SEQUENCE: 5
gtacgatgct gaacgatatc ttcg                                    24

<210> SEQ ID NO 6
<211> LENGTH: 45
<212> TYPE: DNA
<213> ORGANISM: Artificial Sequence
<220> FEATURE:
<223> OTHER INFORMATION: Completely Synthetic DNA Sequence

<400> SEQUENCE: 6
gaatacatgc cgatggaaag cgacggggct gaagagatgg aggtg             45

<210> SEQ ID NO 7
<211> LENGTH: 45
<212> TYPE: DNA
<213> ORGANISM: Artificial Sequence
<220> FEATURE:
<223> OTHER INFORMATION: Completely Synthetic DNA Sequence

<400> SEQUENCE: 7
cccctccatc tcttcagccc cgtcgctttc catcggcatg tattc             45

<210> SEQ ID NO 8
<211> LENGTH: 36
<212> TYPE: DNA
<213> ORGANISM: Artificial Sequence
<220> FEATURE:
<223> OTHER INFORMATION: Completely Synthetic DNA Sequence

<400> SEQUENCE: 8
gaattcagat ctaccatgag cgatgttacc attgtg                       36

<210> SEQ ID NO 9
<211> LENGTH: 30
<212> TYPE: DNA
<213> ORGANISM: Artificial Sequence
<220> FEATURE:
<223> OTHER INFORMATION: Completely Synthetic DNA Sequence

<400> SEQUENCE: 9
tctagatctt attctcgtcc acttgcagag                              30

<210> SEQ ID NO 10
<211> LENGTH: 48
<212> TYPE: DNA
<213> ORGANISM: Artificial Sequence

```
<220> FEATURE:
<223> OTHER INFORMATION: Completely Synthetic DNA Sequence

<400> SEQUENCE: 10
ggtaccatgg aatacatgcc gatggaaagc gatgttacca ttgtgaag                    48

<210> SEQ ID NO 11
<211> LENGTH: 33
<212> TYPE: DNA
<213> ORGANISM: Artificial Sequence
<220> FEATURE:
<223> OTHER INFORMATION: Completely Synthetic DNA Sequence

<400> SEQUENCE: 11
aagcttagat ctaccatgaa tgaggtgtct gtc                                    33

<210> SEQ ID NO 12
<211> LENGTH: 30
<212> TYPE: DNA
<213> ORGANISM: Artificial Sequence
<220> FEATURE:
<223> OTHER INFORMATION: Completely Synthetic DNA Sequence

<400> SEQUENCE: 12
gaattcggat cctcactcgc ggatgctggc                                        30

<210> SEQ ID NO 13
<211> LENGTH: 49
<212> TYPE: DNA
<213> ORGANISM: Artificial Sequence
<220> FEATURE:
<223> OTHER INFORMATION: Completely Synthetic DNA Sequence

<400> SEQUENCE: 13
ggtaccatgg aatacatgcc gatggaaaat gaggtgtctg tcatcaaag                   49

<210> SEQ ID NO 14
<211> LENGTH: 6
<212> TYPE: PRT
<213> ORGANISM: Artificial Sequence
<220> FEATURE:
<223> OTHER INFORMATION: Completely Synthetic Amino Acid Sequence

<400> SEQUENCE: 14

Glu Tyr Met Pro Met Glu
 1               5

<210> SEQ ID NO 15
<211> LENGTH: 13
<212> TYPE: PRT
<213> ORGANISM: Artificial Sequence
<220> FEATURE:
<223> OTHER INFORMATION: Completely Synthetic Amino Acid Sequence

<400> SEQUENCE: 15

Gly Gly Arg Ala Arg Thr Ser Ser Phe Ala Glu Pro Gly
 1               5                   10

<210> SEQ ID NO 16
<211> LENGTH: 15
<212> TYPE: PRT
<213> ORGANISM: Artificial Sequence
```

-continued

```
<220> FEATURE:
<223> OTHER INFORMATION: Completely Synthetic Amino Acid Sequence

<400> SEQUENCE: 16

Lys Lys Gly Gly Arg Ala Arg Thr Ser Ser Phe Ala Glu Pro Gly
1               5                   10                  15
```